US011806453B2

(12) United States Patent
Alvarez et al.

(10) Patent No.: US 11,806,453 B2
(45) Date of Patent: *Nov. 7, 2023

(54) APPARATUS AND METHODS TO CREATE POSTERIOR COMPRESSION AT THE BREAST DURING EXPRESSION OF BREAST MILK

(71) Applicant: WILLOW INNOVATIONS, INC., Mountain View, CA (US)

(72) Inventors: Jeffery B. Alvarez, Redwood City, CA (US); Polina A. Segalova, Redwood City, CA (US)

(73) Assignee: Willow Innovations, Inc., Mountain View, CA (US)

( * ) Notice: Subject to any disclaimer, the term of this patent is extended or adjusted under 35 U.S.C. 154(b) by 955 days.

This patent is subject to a terminal disclaimer.

(21) Appl. No.: 16/661,214

(22) Filed: Oct. 23, 2019

(65) Prior Publication Data
US 2020/0054805 A1 Feb. 20, 2020

Related U.S. Application Data

(63) Continuation of application No. 15/349,917, filed on Nov. 11, 2016, now Pat. No. 10,485,908.

(60) Provisional application No. 62/255,241, filed on Nov. 13, 2015.

(51) Int. Cl.
*A61M 1/06* (2006.01)
*A61M 1/00* (2006.01)

(52) U.S. Cl.
CPC .............. *A61M 1/06* (2013.01); *A61M 1/064* (2014.02); *A61M 1/06935* (2021.05); *A61M 1/82* (2021.05)

(58) Field of Classification Search
CPC ........ A61M 1/06; A61M 1/064; A61M 1/062; A61M 1/066; A61M 1/0697; A61M 1/06935; A61M 2210/1007; A61J 13/00; A61J 9/00
See application file for complete search history.

(56) References Cited

U.S. PATENT DOCUMENTS

| 4,263,912 A | * | 4/1981 | Adams | A61M 1/064 604/75 |
| 4,323,067 A | * | 4/1982 | Adams | A61M 1/06 604/74 |
| 4,799,922 A | * | 1/1989 | Beer | A61M 1/81 604/74 |

(Continued)

FOREIGN PATENT DOCUMENTS

EP 198469 A2 * 4/1986 ............. A61M 1/06

*Primary Examiner* — Scott J Medway

(57) ABSTRACT

Improved devices and methods for the expression of milk from a breast are disclosed herein. A device for expressing breast milk may comprise a breast interface including a flange configured to engage a breast and fluidly seal thereagainst, and an actuatable assembly operably coupled to the breast interface and configured to apply vacuum pressure at the breast interface. The breast interface may be configured to apply anterior compression to an anterior portion of the breast when the actuatable assembly is actuated. The flange may be configured to apply posterior compression to a posterior portion of the breast when the actuatable assembly is actuated. The posterior compression can help improve the efficiency of milk expression by reducing the retrograde flow of milk.

19 Claims, 26 Drawing Sheets

(56) References Cited

U.S. PATENT DOCUMENTS

| | | | |
|---|---|---|---|
| 4,857,051 A | 8/1989 | Larsson | |
| 5,885,246 A * | 3/1999 | Ford | A61M 1/066 604/74 |
| 6,273,868 B1 | 8/2001 | Nordvik | |
| 6,579,258 B1 * | 6/2003 | Atkin | A61M 1/066 604/74 |
| 6,663,587 B2 * | 12/2003 | Silver | A61M 1/066 119/14.47 |
| 6,673,036 B1 | 1/2004 | Britto | |
| 7,875,000 B2 | 1/2011 | Krebs et al. | |
| 8,052,635 B1 | 11/2011 | Kelly et al. | |
| 8,684,961 B2 * | 4/2014 | Gottenbos | A61M 1/066 604/74 |
| 8,992,467 B2 * | 3/2015 | Kobayashi | A61M 1/062 604/74 |
| 9,078,962 B2 * | 7/2015 | Hirata | A61M 1/064 |
| 9,248,223 B2 * | 2/2016 | Van Der Kamp | A61M 1/0697 |
| 10,016,548 B1 | 7/2018 | Quackenbush | |
| 10,105,474 B2 | 10/2018 | Barral et al. | |
| 10,279,091 B1 * | 5/2019 | Jones | A61M 1/064 |
| 10,758,653 B2 * | 9/2020 | Kumar | A61H 9/0057 |
| 11,116,880 B2 * | 9/2021 | Quackenbush | A61M 1/064 |
| 11,413,381 B2 * | 8/2022 | Quackenbush | A61M 1/066 |
| 2002/0198489 A1 | 12/2002 | Silver et al. | |
| 2003/0073951 A1 | 4/2003 | Morton et al. | |
| 2003/0191433 A1 * | 10/2003 | Prentiss | A61M 1/062 604/74 |
| 2005/0154349 A1 * | 7/2005 | Renz | A61M 1/0697 604/74 |
| 2005/0234370 A1 | 10/2005 | Beal et al. | |
| 2006/0106334 A1 | 5/2006 | Jordan et al. | |
| 2010/0130921 A1 | 5/2010 | Kobayashi et al. | |
| 2011/0004155 A1 | 1/2011 | Tashiro | |
| 2011/0071466 A1 * | 3/2011 | Silver | A61M 1/0697 604/74 |
| 2012/0004604 A1 | 1/2012 | Van et al. | |
| 2014/0031744 A1 * | 1/2014 | Chen | A61M 1/06 604/74 |
| 2014/0121593 A1 | 5/2014 | Felber et al. | |
| 2014/0288466 A1 | 9/2014 | Alvarez et al. | |
| 2015/0065994 A1 | 3/2015 | Fridman et al. | |
| 2015/0283311 A1 | 10/2015 | Alvarez et al. | |
| 2016/0000982 A1 | 1/2016 | Alvarez et al. | |
| 2016/0206794 A1 | 7/2016 | Makower et al. | |
| 2017/0072118 A1 | 3/2017 | Makower et al. | |
| 2017/0080134 A1 | 3/2017 | Makower et al. | |
| 2017/0136161 A1 | 5/2017 | Alvarez et al. | |
| 2017/0173232 A1 | 6/2017 | Chang et al. | |
| 2018/0078687 A1 | 3/2018 | Alvarez et al. | |
| 2018/0154055 A1 | 6/2018 | Alvarez et al. | |

* cited by examiner

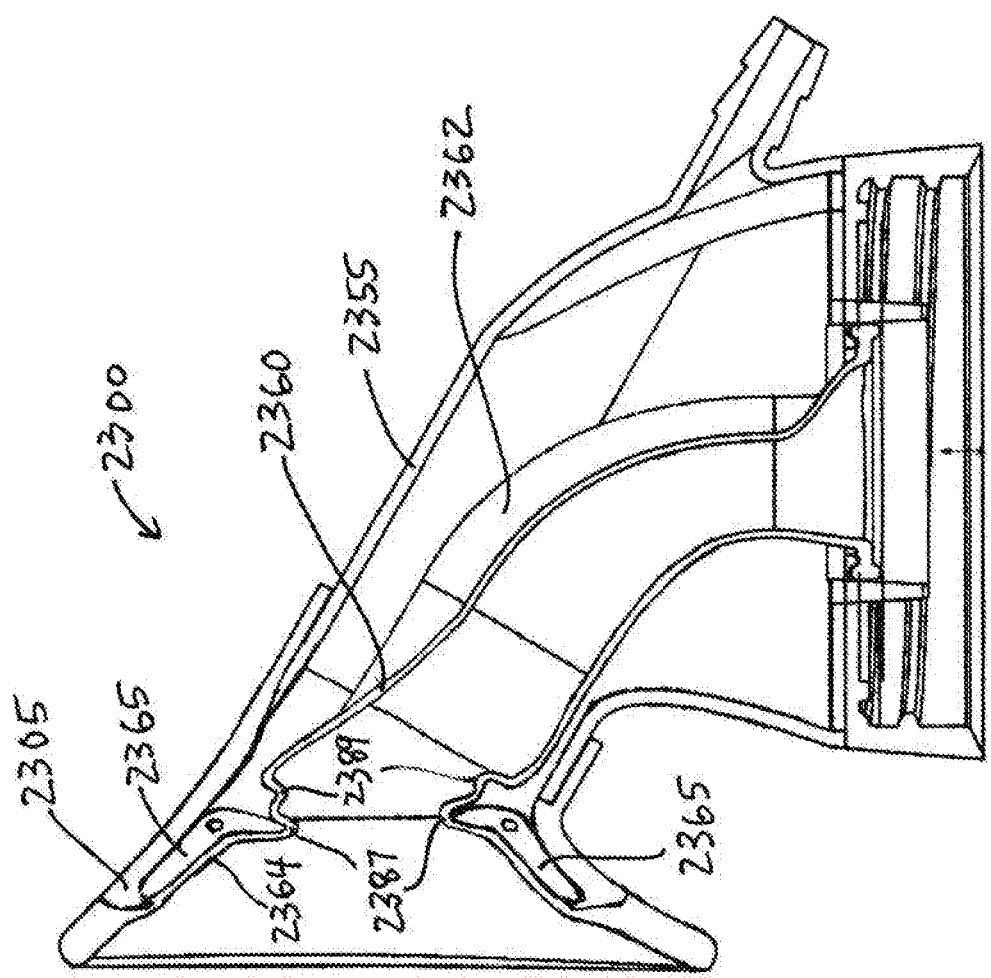

APPARATUS AND METHODS TO CREATE POSTERIOR COMPRESSION AT THE BREAST DURING EXPRESSION OF BREAST MILK

CROSS-REFERENCE

The present application is a non-provisional of, and claims the benefit of, U.S. Provisional Patent Application 62/255,241, filed on Nov. 13, 2015, and a continuation of U.S. application Ser. No. 15/349,917, filed Nov. 11, 2016, the entire contents of which are incorporated herein by reference.

This application is also related to the following co-pending patent applications: U.S. application Ser. No. 14/221,113, filed Mar. 20, 2014; U.S. application Ser. No. 14/616,557, filed Feb. 6, 2014; U.S. application Ser. No. 14/793,606, filed Jul. 7, 2015; U.S. application Ser. No. 14/793,613, filed Jul. 7, 2015; U.S. application Ser. No. 14/793,617, filed Jul. 7, 2015; U.S. application Ser. No. 14/858,924, filed Sep. 18, 2015; U.S. application Ser. No. 15/094,690, filed Apr. 8, 2016; and U.S. application Ser. No. 15/094,704, filed Apr. 8, 2016, the entire discloses of which are incorporated herein by reference.

BACKGROUND OF THE INVENTION

Breast pumps are commonly used to collect breast milk in order to allow mothers to continue breastfeeding while apart from their children. Breast pumps typically express milk from the mammary glands of the breast by creating a vacuum in the neck portion of a funnel-shaped component commonly referred to as the flange or the breast interface. The vacuum pulls the nipple and portions of the areola into the flange neck, causing compression of anterior portions of the breast tissue against portions of the breast interface. By contrast, a baby applies light vacuum and compression of posterior portions of the breast tissue using peristaltic motion of the jaws, lips, and/or tongue, wherein the posterior compression helps prevent retrograde flow of the breast milk and achieve more efficient and comfortable milk expression.

It would be desirable to provide a breast pump that can better mimic aspects of milk expression during natural nursing, to improve the efficiency of milk expression and the comfort of the user during pumping. Ideally, such a breast pump can help prevent retrograde flow of the milk and stimulate expression of additional milk.

At least some of these objectives will be satisfied by the devices and methods disclosed below.

SUMMARY OF THE INVENTION

Improved devices and methods for the expression of milk from a breast are disclosed herein. A device for expressing breast milk may comprise a mechanism to apply anterior compression to an anterior portion of the breast, and posterior compression to a posterior portion of the breast when the actuatable assembly is actuated and negative pressure is applied at the breast interface. For example, a breast interface of an expression device, configured to generate vacuum pressure at the breast interface and thereby apply the anterior compression, may comprise one or more movable members or actuatable elements configured to apply the posterior compression. The posterior compression of the breast can apply additional compression on posterior portions of the milk ducts after the anterior compression has pushed some milk out of the ducts. This additional compression can not only help prevent some retrograde flow of milk back towards the alveoli of the mammary glands, but also help express more hind milk. In addition to the helping to improve expression efficiency, a mechanism as described herein for providing posterior compression of the breast can also mimic the peristaltic motion of a nursing baby's jaws, lips, and/or tongue, thus providing a more comfortable experience for the user during pumping.

In one aspect, a device for expression of breast milk from a breast comprises a breast interface and an actuatable assembly operably coupled to the breast interface. The breast interface comprises a flange configured to engage the breast and fluidly seal thereagainst. The actuatable assembly is configured to generate negative pressure at the breast interface when actuated. The flange comprises a movable member having an anterior portion and a posterior portion, the anterior portion configured to engage an anterior portion of the breast and the posterior portion configured to engage a posterior portion of the breast when the breast is fluidly sealed against the flange. The anterior portion of the movable member is configured to apply anterior compression to the breast in response to generation of negative pressure at the breast interface. Further, the movable member is configured to move in response to the anterior compression of the breast against the anterior portion of the movable member, to subsequently apply posterior compression to the breast with the posterior portion of the movable member.

The anterior portion of the movable member may be configured to move away from the breast and the posterior portion of the movable member may be configured to move towards the breast in response to generation of negative pressure at the breast interface. The movable member may be configured to apply the anterior compression and the posterior compression in a temporally coupled manner, such that, when the negative pressure is applied at the breast interface, the anterior compression is applied first and the posterior compression is applied second.

The movable member may be a lever, wherein the lever may be configured to rotate about a pivot point to apply the posterior compression to the breast. The lever may be coupled to an interior surface of the flange via the pivot point. The anterior portion of the lever may comprise a first arm of the lever and the posterior portion of the lever may comprise a second arm of the lever, wherein the first and second arms may be joined about the pivot point. The first arm may be configured to apply the anterior compression and the second arm may be configured to apply the posterior compression to the breast. The lever may be configured such that a moment generated about the first arm in a first direction by the anterior compression of the breast against the first arm is greater than a moment generated about the second arm in a second direction opposite the first direction by the posterior compression of the breast against the second arm. A longitudinal axis of the first arm and a longitudinal axis of the second arm may be non-collinear. A length of the first arm may be different from a length of the second arm.

The lever may comprise a substantially rigid member of the flange coupled to a flexible member of the flange. The substantially rigid member of the flange may be configured to rotate about the pivot point to apply the posterior compression, wherein the pivot point may be disposed near an anterior portion of the substantially rigid member. The flexible member may comprise an anterior portion configured to bend in response to compression of the breast against the lever. The substantially rigid member may be configured to rotate about the pivot point in response to the bending of the anterior portion of the flexible member.

The device may further comprise a flexible cover disposed over the lever to enclose the lever. The flexible cover may be configured to fluidly seal against the breast and to allow rotation of the lever within the cover, thereby reducing pinching of the breast by the lever during rotation.

The anterior compression of the breast may cause retrograde flow of at least a portion of milk in a milk duct of the breast in a direction away from a nipple of the breast. The posterior compression of the breast may reduce the retrograde flow of milk.

The flange may comprise a plurality of movable members distributed annularly about the flange. Alternatively, the movable member may comprise a single, continuous movable member extending annularly about the flange.

The breast interface may further comprise a housing and a membrane disposed within and coupled to the housing. The membrane may comprise an expandable portion configured to move toward the housing and away from the breast in response to actuation of the actuatable assembly to apply negative pressure at the breast interface. The membrane may comprise a flexible cover portion disposed over the movable member to enclose the movable member. The flexible cover portion may be configured to fluidly seal against the breast and to allow movement of the movable member within the flexible cover portion. The membrane may be shaped to form the flange, wherein the movable member may comprise a substantially rigid portion of the flange. The substantially rigid portion of the flange may comprise a thickness that is greater than a thickness of the membrane at the expandable portion. The substantially rigid portion of the flange may be configured to rotate about a pivot point disposed near an anterior portion of the substantially rigid portion of the flange, thereby applying the posterior compression to the breast.

In another aspect, a method for expression of breast milk from a breast comprises providing a breast milk expression device comprising a breast interface and an actuatable assembly operably coupled thereto. The method further comprises engaging the breast within a flange of the breast interface, and actuating the actuatable assembly to generate negative pressure at the breast interface. The method further comprises applying anterior compression to an anterior portion of the breast with a movable member of the flange. The method further comprises applying posterior compression to a posterior portion of the breast with the movable member of the flange by moving the movable member in response to the anterior compression of the breast against the movable member.

The method may comprise moving an anterior portion of the movable member away from the breast and moving a posterior portion of the movable member towards the breast in response to generation of negative pressure at the breast interface. The steps of applying the anterior compression and applying the posterior compression may be temporally coupled, such that when negative pressure is generated at the breast interface, the anterior compression is applied first and the posterior compression is applied second.

The movable member of the flange may comprise a lever configured to rotate about a pivot point. Applying the posterior compression may comprise rotating the lever about the pivot point to apply the posterior compression to the breast. The lever may comprise a first arm and a second arm joined about the pivot point. Applying the anterior compression may comprise compressing the first arm against the anterior portion of the breast, and applying the posterior compression may comprise rotating the lever about the pivot point to compress the second arm against the posterior portion of the breast.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 23 illustrates another exemplary embodiment of a posterior compression mechanism.

DETAILED DESCRIPTION OF THE INVENTION

Specific embodiments of the disclosed systems, devices, and methods will now be described with reference to the drawings. Nothing in this detailed description is intended to imply that any particular component, feature, or step is essential to the invention. Although the present invention primarily relates to breast milk, any description herein of expression and collection of breast milk can also be applied to other types of fluids expressed from the breast, such as colostrum, or from other glands, organs, or anatomical regions of the body.

Figure 1:
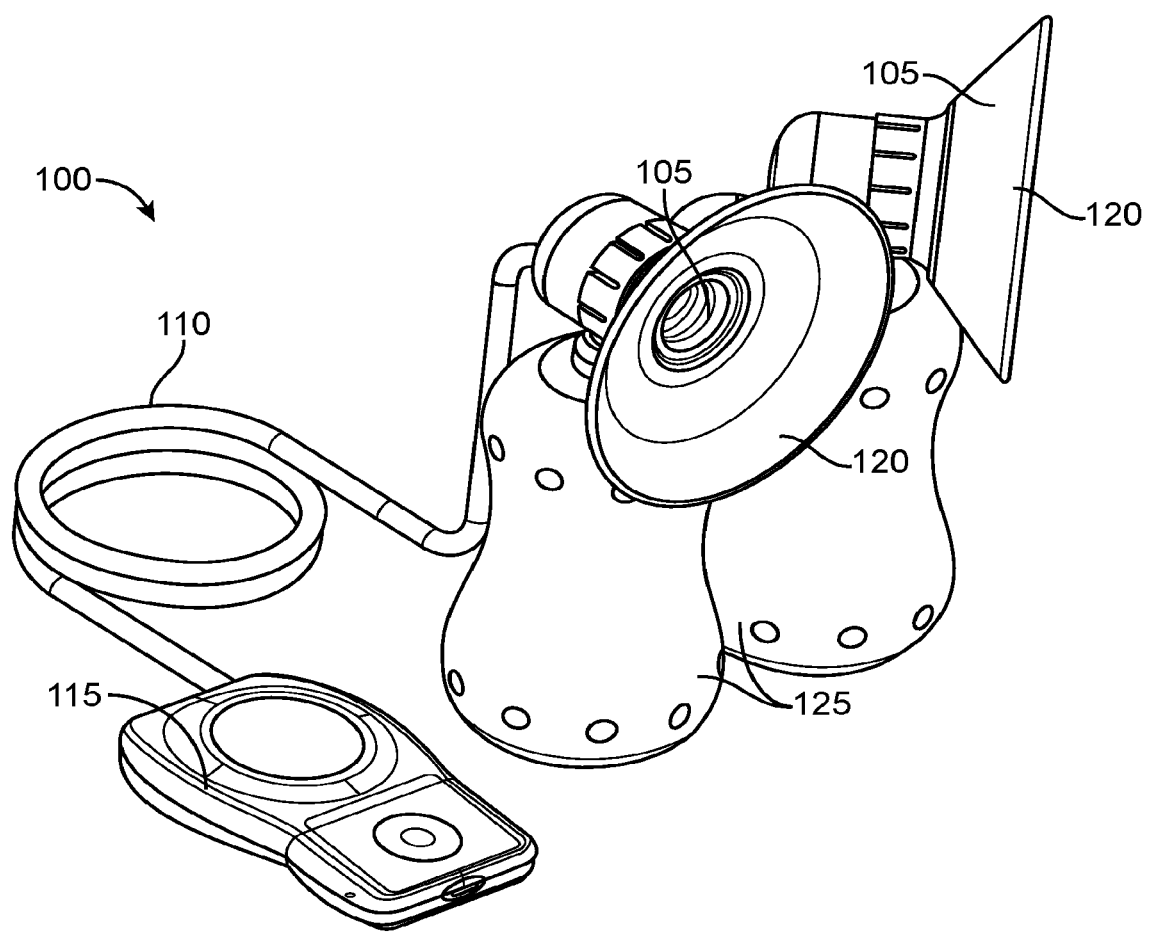
FIG. 1 is a perspective view of an exemplary embodiment of a pumping device.

FIG. 1 illustrates an exemplary embodiment of a breast pump. Pumping device 100 includes breast interfaces 105, a tube 110, and a controller or pendant unit 115 operatively coupled to breast interfaces 105 through tube 110. Breast interfaces 105 include resilient and conformable flanges 120, for engaging and creating a fluid seal against the breasts, and collection vessels 125. The device may optionally only have a single breast interface. Pendant unit 115 houses the power source and drive mechanism for pumping device 100, and also contains hardware for various functions, such as controlling pumping device 100, milk production quantification and content analysis, and communication with other devices. Tube 110 transmits suitable energy inputs, such as mechanical energy inputs, from pendant unit 115 over a long distance to breast interfaces 105. Breast interfaces 105 convert the energy inputs into vacuum pressure against the breasts in a highly efficient manner, resulting in the expression of milk into collection vessels 125.

One of skill in the art will appreciate that components and features of this exemplary embodiment can be combined or substituted with components and features of any of the embodiments of the present invention as described below. Similarly, components and features of other embodiments disclosed herein may be substituted or combined with one another.

Hydraulic Pumping Device

Hydraulic systems can reduce pumping force requirements, and therefore also reduce the size of the pumping device, while maintaining high pumping efficiency. In a preferred embodiment, the pumping device can utilize a hydraulic pumping device to generate a pressure differential against the breast for the expression and collection of milk.

Figure 2:
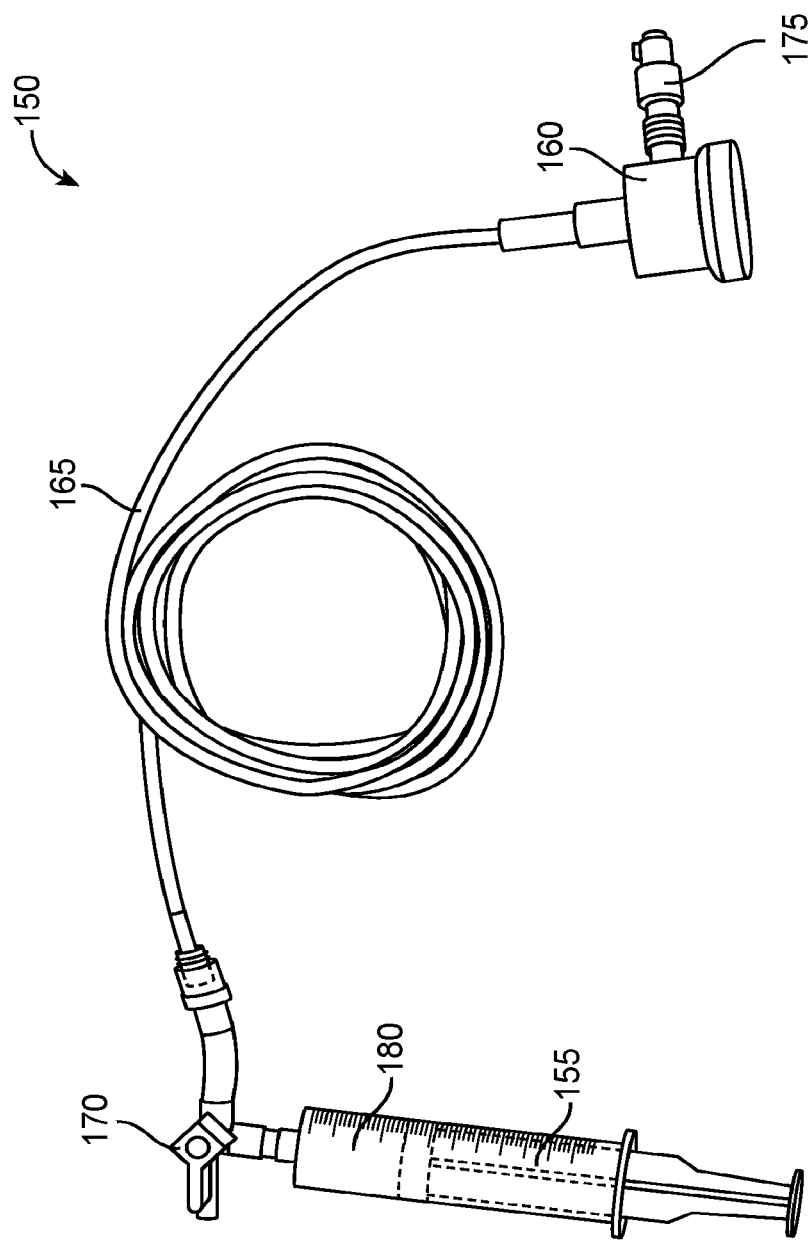
FIG. 2 is a perspective view of an exemplary embodiment of a pumping device.

Exemplary hydraulic pumping devices are depicted in FIGS. 2 and 3. FIG. 2 illustrates a pumping device 150 with a syringe 155 fluidly coupled to breast interface 160 by tube 165. Syringe 155 is coupled to tube 165 through a three-way valve 170. Breast interface 160 contains an exit port 175. The syringe 155 drives a fluid 180 contained within tube 165 against or away from an expandable member contained within breast interface 160 to create the pressure differential necessary for milk expression from the breast.

Figure 3A:
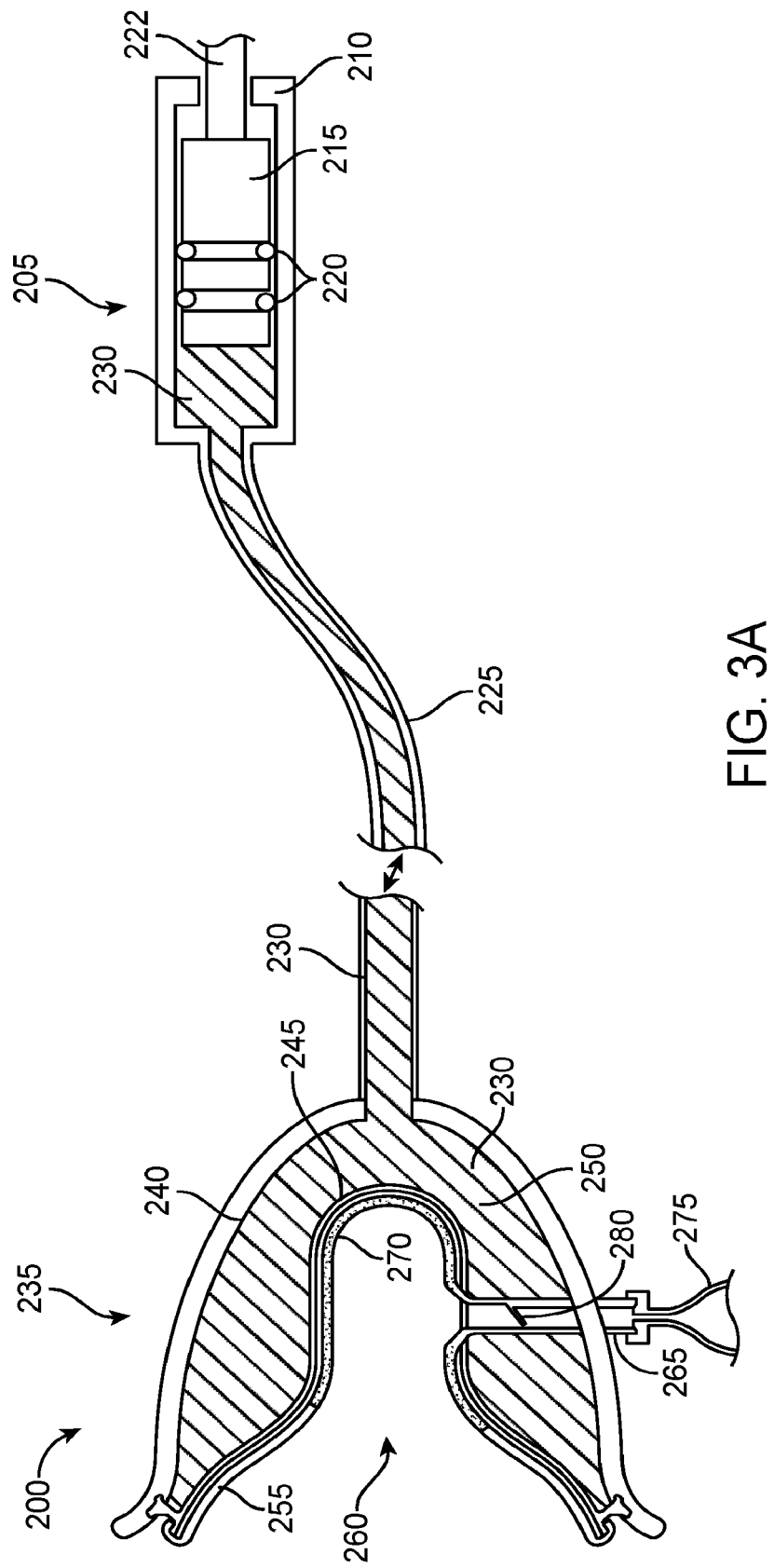
FIGS. 3A-3B show a cross-section of an exemplary embodiment of a pumping device.

FIG. 3A illustrates another embodiment of a pumping device 200. The actuatable assembly 205 includes an assembly housing 210, a driving element 215, radial seals 220, and a shaft 222. Driving element 215 is operatively coupled to a pendant unit, such as pendant unit 115, through shaft 222. The tube 225 contains a fluid 230 and is fluidly coupled to the actuatable assembly 205 and the breast interface 235. The breast interface 235 consists of an interface housing 240, a flexible membrane 245, a reservoir 250, a sealing element 255, an expression area 260, and a drain port 265. The sealing element 255 includes deformable portion 270. The drain port 265 is coupled to a collection vessel 275 and includes a one-way valve 280 which may be a flap, duckbill, or ball valve.

Actuatable assembly 205 displaces fluid 230 contained within tube 225, which can be a flexible line. Fluid 230 occupies reservoir 250 within breast interface 235 and is coupled with flexible membrane 245. Flexible membrane 245 transmits vacuum pressure from fluid 230 to the deformable portion 270 of sealing element 255. The flexible membrane 245 and deformable portion 270 are movable so as to move toward and away from the breast as the actuatable element 215 is actuated. When a breast is engaged into and fluidly sealed with breast interface 235 by sealing element 255, displacement of the actuatable element 215 in the outward direction away from the breast produces substantial vacuum pressure against the breast through flexible membrane 245 and deformable portion 270, resulting in the expression of breast milk into expression area 260. The expressed milk drains through drain port 265 into collection vessel 275. Drain port 265 is configured with a one-way valve 280 to provide passage of milk while maintaining vacuum pressure in expression area 260.

Figure 3B:
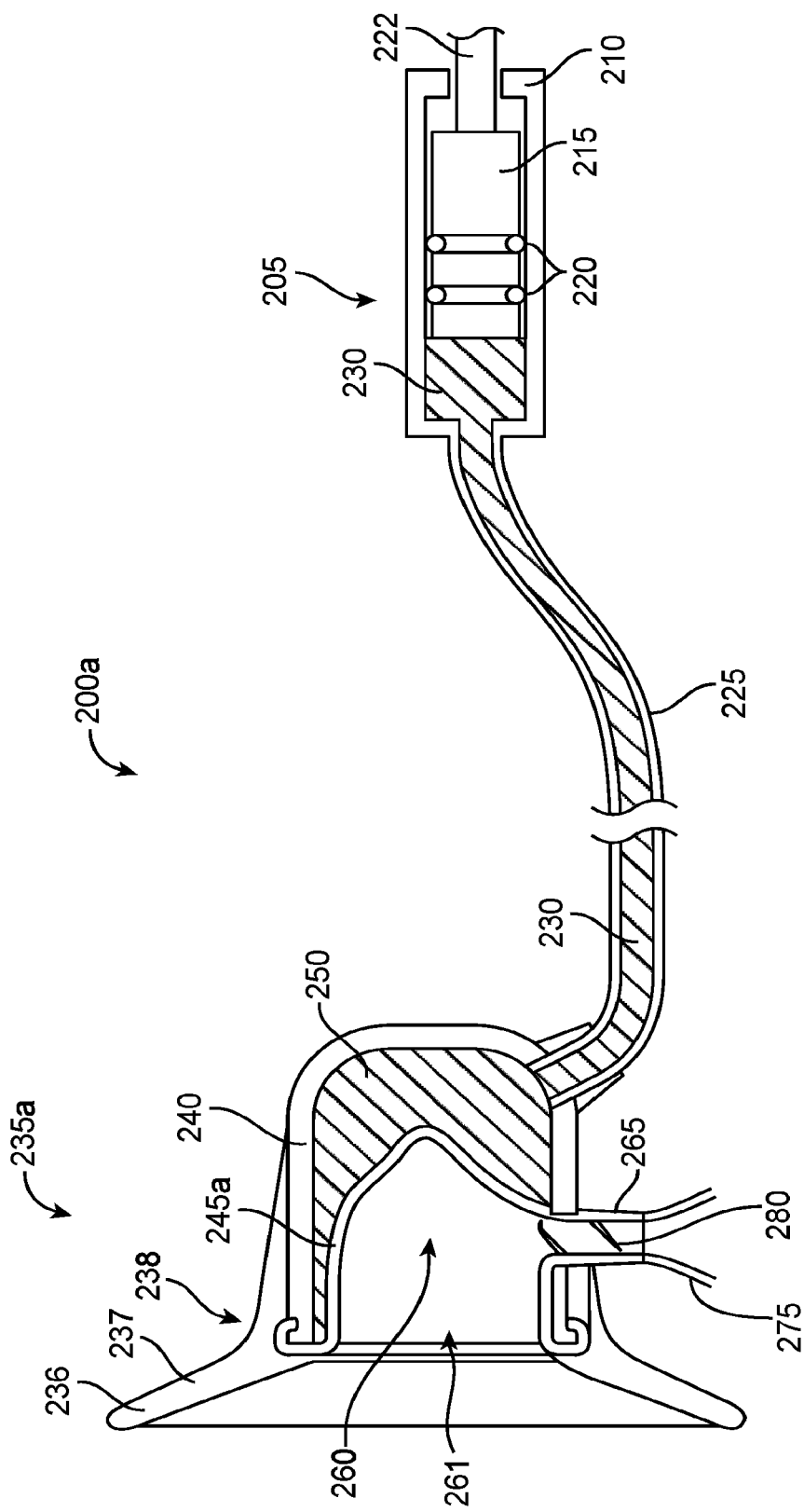

FIG. 3B illustrates another exemplary embodiment of a pumping device 200a. The actuatable assembly 205 includes an assembly housing 210, a driving element 215, radial seals 220, and a shaft 222. Driving element 215 is operatively coupled to a pendant unit, such as pendant unit 115, through shaft 222. The tube 225 contains a fluid 230 and is fluidly coupled to the actuatable assembly 205 and the breast interface 235a. The breast interface 235a comprises a flange 236, an interface housing 240, an expandable membrane 245a, an expression reservoir 250, an expression area 260, and a drain port 265. The flange 236 comprises a frustoconical portion 237 and a tubular flange neck 238. The flange neck connects to the expression area through the expression mouth 261. The drain port 265 is coupled to a collection vessel 275 and includes a one-way valve 280.

Actuatable assembly 205 displaces fluid 230 contained within tube 225, which can be a flexible line. Fluid 230 occupies expression reservoir 250 within breast interface 235a and is coupled with expandable membrane 245a. The expandable membrane 245a is movable so as to move toward and away from the breast as the actuatable element 215 is actuated. When a breast is engaged into and fluidly sealed with breast interface 235a by the flange 236, displacement of the actuatable element 215 in the outward direction away from the breast produces substantial vacuum pressure against the breast through expandable membrane 245a, resulting in the expression of breast milk into expression area 260. The expressed milk drains through drain port 265 into collection vessel 275. Drain port 265 is configured with a one-way valve 280 to provide passage of milk while maintaining vacuum pressure in expression area 260.

The fluid for the hydraulic pumping device can be any suitable fluid, such as an incompressible fluid. In many embodiments, the incompressible fluid can be water or oil. Alternatively, the fluid can be any suitable gas, such as air. Suitable incompressible fluids and gases for hydraulic systems are known to those of skill in the art.

One of skill in the art will appreciate that components and features of any of the exemplary embodiments of the hydraulic pumping device can be combined or substituted with components and features of any of the embodiments of the present invention as described herein.

Actuation Mechanism

Many actuation mechanisms known to those of skill in the art can be utilized for the actuatable assembly 205. Actuatable assembly 205 can be a piston assembly, a pump such as a diaphragm pump, any other suitable actuation mechanism or pump mechanism, or any combination of the above. The optimal configuration for actuatable assembly 205 can depend on a number of factors, such as: vacuum requirements; size, power, and other needs of the pumping device 200; and the properties of the fluid 230, such as viscosity, biocompatibility, and fluid life requirements.

FIGS. 3A and 3B illustrate exemplary embodiments in which actuatable assembly 205 is a piston assembly and driving element 215 is a piston. Actuatable assembly 205 includes radial seals 220, such as O-rings, sealing against assembly housing 210 to prevent undesired egress of fluid 230 and to enable driving of fluid 230. Other sealing mechanisms and other driving mechanisms as known or yet to be developed by one of skill in the art may be used to prevent undesired egress of fluid and to enable the driving of fluid respectively.

Figure 4:
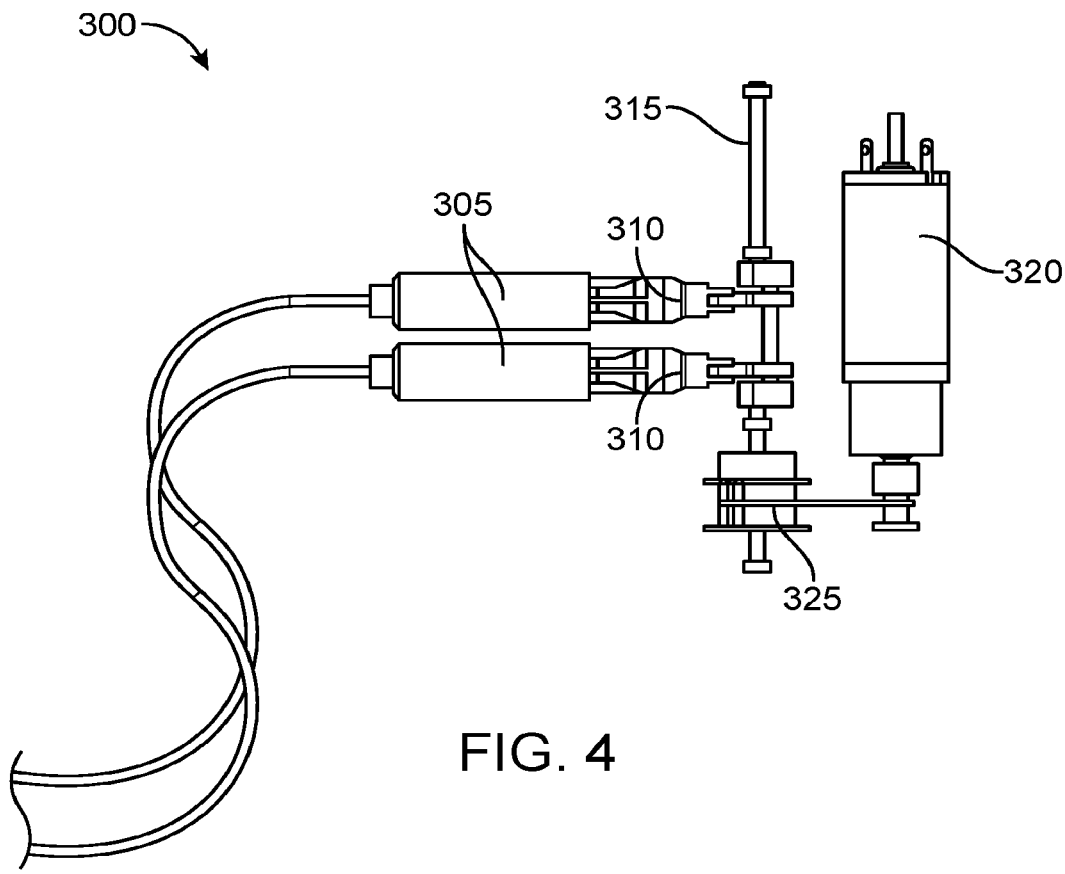
FIG. 4 illustrates an exemplary embodiment of an actuatable assembly coupled to a driving mechanism.

FIG. 4 illustrates another exemplary embodiment of an actuatable assembly 300 including a pair of pistons 305.

In preferred embodiments, the actuatable assembly includes a driving element powered by a suitable driving mechanism, such as a driving mechanism residing in pendant unit 115. Many driving mechanisms are known to those of skill in the art. For instance, the driving element, such as driving element 215, may be actuated electromechanically by a motor, or manually by a suitable user-operated interface, such as a lever. Various drive modalities known to those of skill in the art can be used. In particular, implementation of the exemplary hydraulic pumping devices as described herein enables the use of suitable drive modalities such as direct drive and solenoids, owing to the reduced force requirements of hydraulic systems.

Referring now to the exemplary embodiment of FIG. 4, the pistons 305 include couplings 310 to a crankshaft 315. The crankshaft 315 is operatively coupled to a motor 320 through a belt drive 325. The crankshaft 315 drives the pair of pistons 305 with the same stroke timing in order to apply vacuum pressure against both breasts simultaneously, a feature desirable for increased milk production. Alternatively, the crankshaft 315 can drive the pair of pistons 305 with any suitable stroke timing, such as alternating or offset stroke cycles.

The driving mechanism can be powered by any suitable power source, such as a local battery or an AC adaptor. The driving mechanism can be controlled by hardware, such as onboard electronics located within pendant unit 115.

Figure 5A:
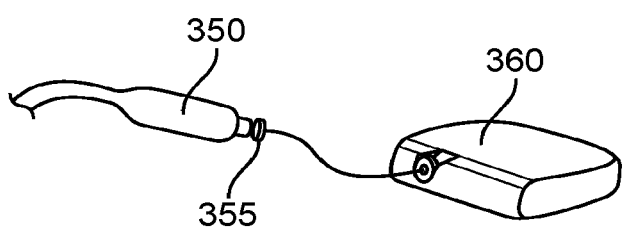
FIGS. 5A-5B illustrate an exemplary embodiment of an actuatable assembly coupled to a pendant unit.
Figure 5B:
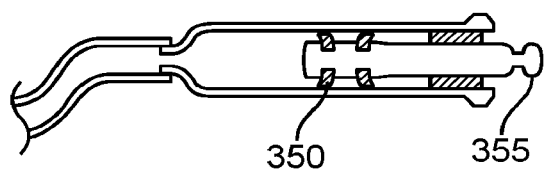

FIGS. 5A-5B illustrate an exemplary embodiment of an actuatable assembly 350 that includes releasable coupling 355. FIG. 5A is a perspective view of the embodiment, and FIG. 5B is a cross-sectional view of the embodiment. Preferably, actuatable assembly 350 is releasably coupled to a pendant unit 360 and the driving mechanism housed therein. The coupling can be a mechanical coupling or any suitable quick release mechanism known to those of skill in the art. The releasably coupled design allows for flexibility in the configuration and use of the pumping device. For instance, user comfort can be improved through the use of differently sized breast interfaces for compatibility with various breast sizes. Additionally, this feature enables a common pumping device to be used with interchangeable breast interfaces, thus reducing the risk of spreading pathogens. Furthermore, the releasable coupling enables easy replacement of individual parts of the pumping device.

One of skill in the art will appreciate that components and features of any of the exemplary embodiments of the actuation mechanism can be combined or substituted with components and features of any of the embodiments of the present invention as described herein.

Expandable Membrane

In many embodiments such as the embodiment depicted in FIG. 3B, the expandable membrane 245a is located within breast interface 235a and disposed over at least a portion thereof, forming expression reservoir 250 between the interface housing 240 and the expandable membrane 245a. Preferably, the expandable membrane 245a comprises a resilient material that deforms substantially or a more rigid material that is displaced when subject to the negative pressures created when the fluid 230 is displaced from expression reservoir 250 by actuatable assembly 205. The expandable membrane returns to an unbiased position when the negative pressures subside. The amount of deformation of the expandable membrane 245a can be controlled by many factors, (e.g., wall thickness, durometer, surface area) and can be optimized based on the pumping device (e.g., pump power, vacuum requirements).

Figure 6:
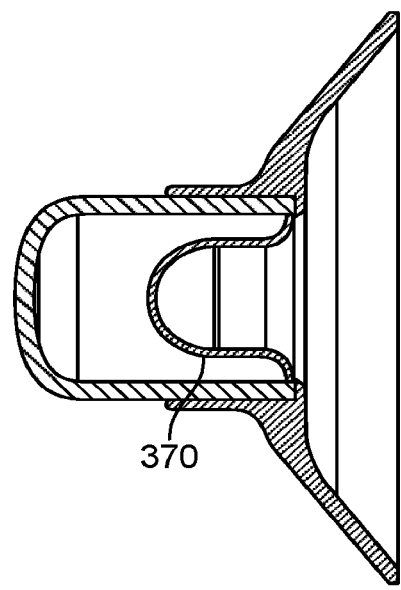
FIG. 6 is a cross-sectional view of an exemplary embodiment of a breast interface.

FIG. 6 illustrates an exemplary expandable membrane 370 with a specified thickness and durometer.

Figure 7:
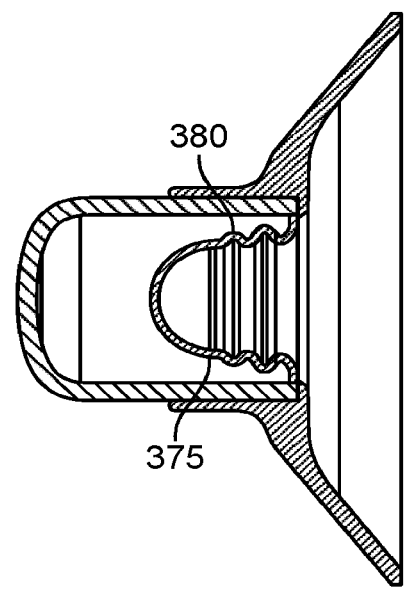
FIG. 7 is a cross-sectional view of another exemplary embodiment of a breast interface.

FIG. 7 illustrates another embodiment of expandable membrane 375 with corrugated features 380 for increased surface area. Other configurations of the expandable membrane which may be used in any of the embodiments of breast pumps described herein are disclosed in U.S. Patent Provisional Application No. 62/021,597 filed Jul. 7, 2014; the entire contents of which are incorporated herein by reference.

Suitable materials for the expandable membrane are known to those of skill in the art. In many embodiments, the expandable membrane can be made of a material designed to expand and contract when subject to pressures from the coupling fluid such as silicone, polyether block amides such as PEBAX, and polychloroprenes such as neoprene or any other substantially expandable material known or yet to be developed by one of skill in the art. Alternatively, the expandable membrane can be fabricated from a substantially rigid material, such as stainless steel, nitinol, high durometer polymer, or high durometer elastomer or any other substantially rigid material known or yet to be developed by one of skill in the art. In these embodiments, the rigid material can be designed with stress and/or strain distribution elements to enable the substantial deformation of the expandable membrane without surpassing the yield point of the material.

Figure 8A:
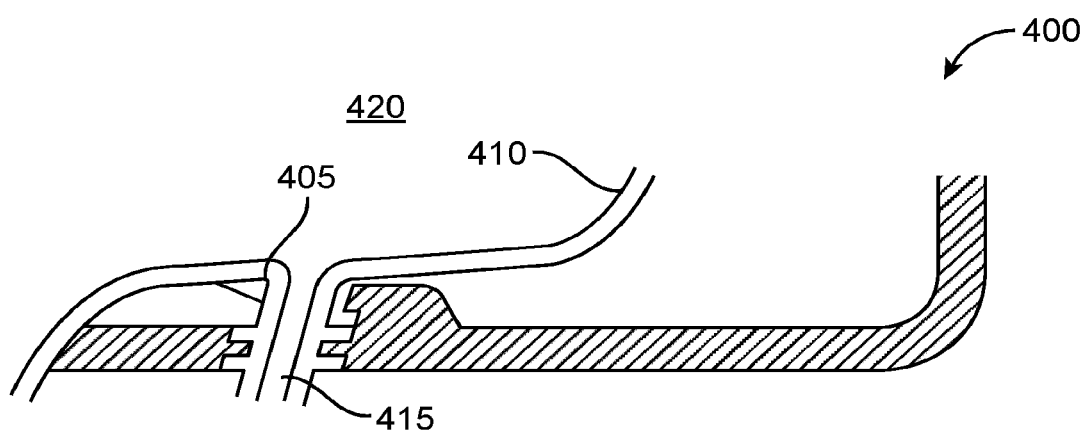
FIG. 8A is a cross-sectional view of an exemplary embodiment of an integrated valve in an open position.
Figure 8B:
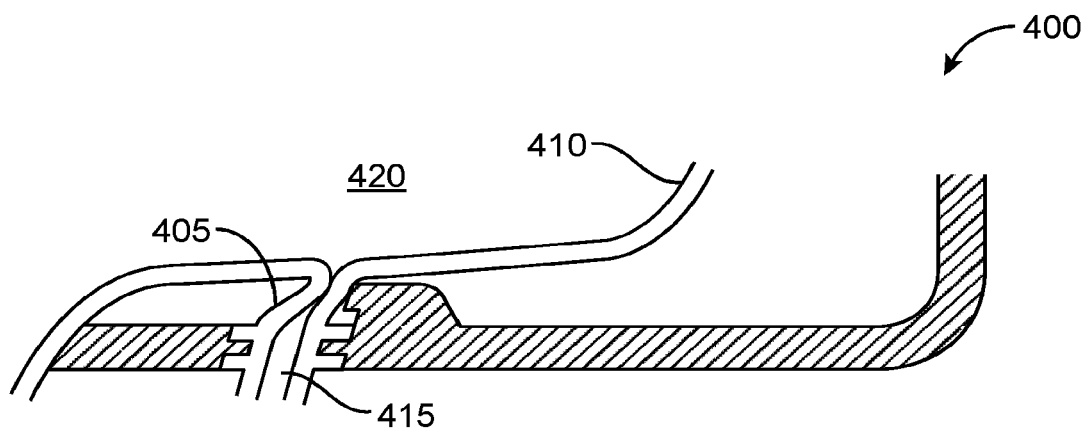
FIG. 8B is a cross-sectional view of an exemplary embodiment of an integrated valve in a closed position.

FIGS. 8A and 8B illustrate preferred embodiments of a breast interface 400 in which an exit valve 405 is integrated into the expandable membrane 410 to control the flow of expressed milk through exit port 415. The exit valve 405 is opened to allow fluid flow when the expandable membrane 410 is relaxed, as shown in FIG. 8A, and is closed to prevent fluid flow when the expandable membrane 410 is deformed, as shown in FIG. 8B. The exit valve 405 enables substantial vacuum pressure to be present in expression area 420 during extraction, while allowing milk to drain during the rest phase of the pump stroke. While many conventional breast pump valves function on pressure differentials alone, the exit valve 405 can preferably be configured to also function on the mechanical movement of expandable membrane 410. Incorporation of an integrated exit valve 405 with mechanical functionality as described herein can improve the sealing of the breast interface 400 during vacuum creation. Furthermore, the implementation of an exit valve integrally formed within the expandable membrane 410 such as exit valve 405 reduces the number of parts to be cleaned. In addition, other control mechanisms that allow fluid flow when the expandable membrane is relaxed and limit or prevent fluid flow when the expandable membrane is deformed may be used to control the flow of expressed milk through the exit port.

One of skill in the art will appreciate that components and features of any of the exemplary embodiments of the expandable membrane can be combined or substituted with components and features of any of the embodiments of the present invention as described herein.

Radially Pleated Membrane

As discussed and best illustrated in FIG. 3, a drain port 265 and flap valve 280 may be coupled to the flexible membrane in order to allow milk to flow into collection vessel 275. Thus, as the flexible membrane is actuated and advanced and retracted, the drain portion 265 and flap valve 280 will typically also move forward and backward. This can cause unwanted stress on the junction between the drain port 265 and the membrane and the collection vessel 275 may also experience unwanted movement. Therefore, it may be desirable to isolate the drain port 265 and flap valve 280 from the membrane so that when the membrane is actuated, other portions of the device experience little or no unwanted motion.

Figure 12A:
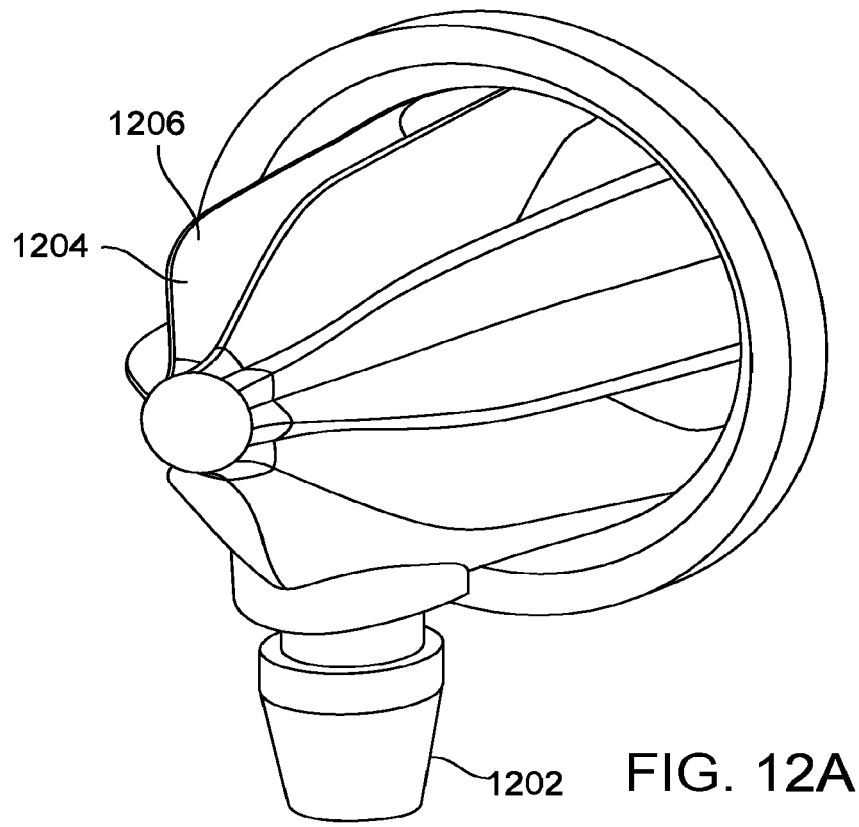
FIG. 12A illustrates an exemplary embodiment of flexible radial bellows.

FIG. 12A illustrates an exemplary embodiment of an expandable membrane that overcomes at least some of these challenges. The expandable membrane 1204 includes a plurality of expandable pleats 1206 that extend radially outward from the center of the expandable membrane. The pleats also have a longitudinal axis which runs substantially parallel to the longitudinal axis of the membrane, and the pleats extend around the circumference of the membrane. The spout or drain port 1202 is disposed along a bottom portion of the membrane in between pleats or in a section of the membrane having no pleats. Thus, actuation of the membrane will expand and contract the membrane radially outward and radially inward and axial motion along a longitudinal axis of the membrane will be minimized and substantially less than previous embodiments. Therefore, the spout or drain port 1202 will remain substantially stationary during actuation of membrane 1204, and the drain port will be substantially free of loads during expansion or contraction of the membrane.

Figure 12B:
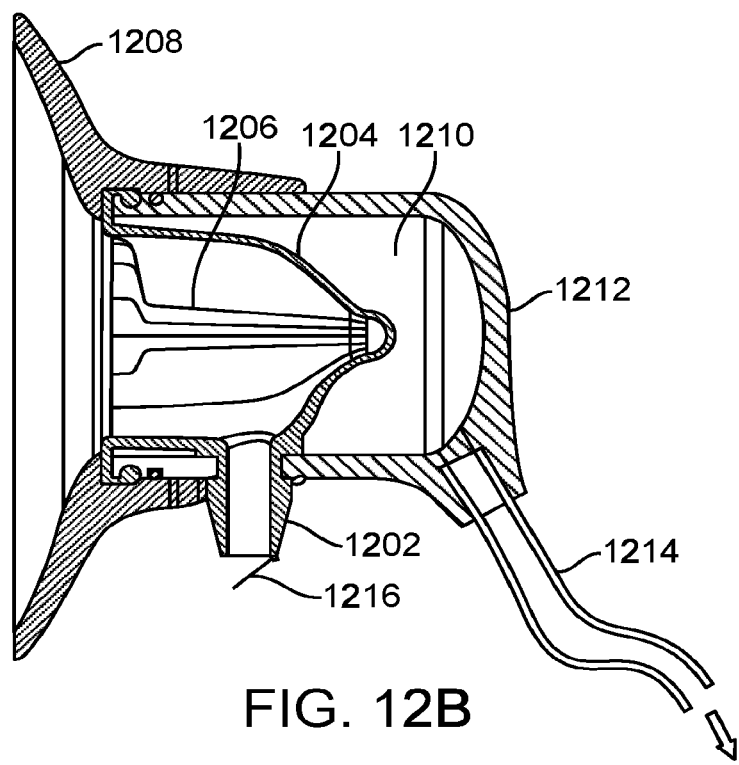
FIG. 12B illustrates a partial cross-section of a breast interface with the bellows in of FIG. 12A.

FIG. 12B illustrates a cross-section of the breast interface which includes a flange 1208, the membrane 1204 with pleats 1206, output spout 1202 and housing 1212. The flange 1208 comprises a resilient material that allows the breast interface to be fluidly sealed against the breast. After collection, the expressed milk drains from output spout 1202 past valve 1216 into a collection vessel. A fluid reservoir 1210 is behind the membrane 1204 and fluid is pulled out to create a vacuum and pushed in to return to normal atmospheric pressure or to a positive pressure. The fluid is hydraulically displaced by movement of fluid in tubing 1214. Fluid movement in the tubing is actuated by any of the pumps or mechanisms disclosed in this specification. As previously discussed, a lower portion of the membrane does not substantially move in the axial direction, thereby holding the drain port or spout in a fixed axial position. This portion also may not move in the radial direction if there are no pleats in that section.

Figure 13A:
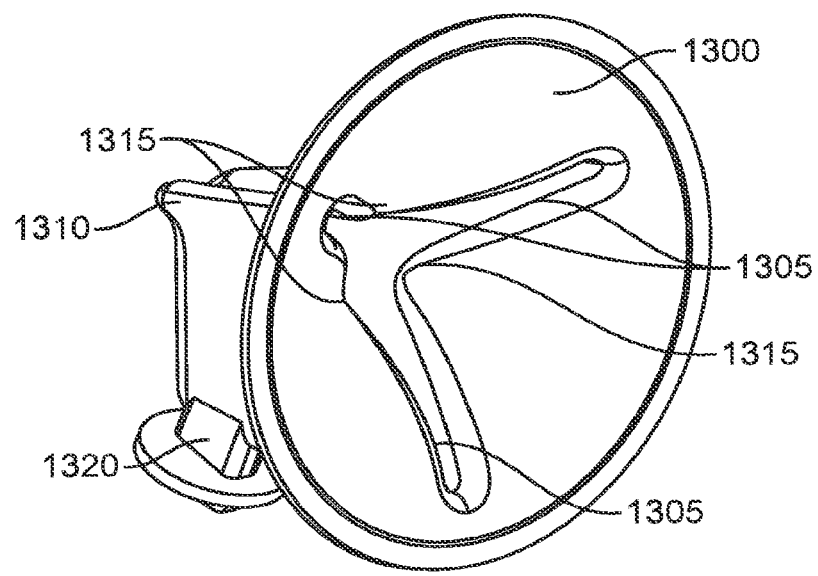
FIGS. 13A-13B illustrate another exemplary embodiment of an expandable membrane having radial pleats.
Figure 13B:
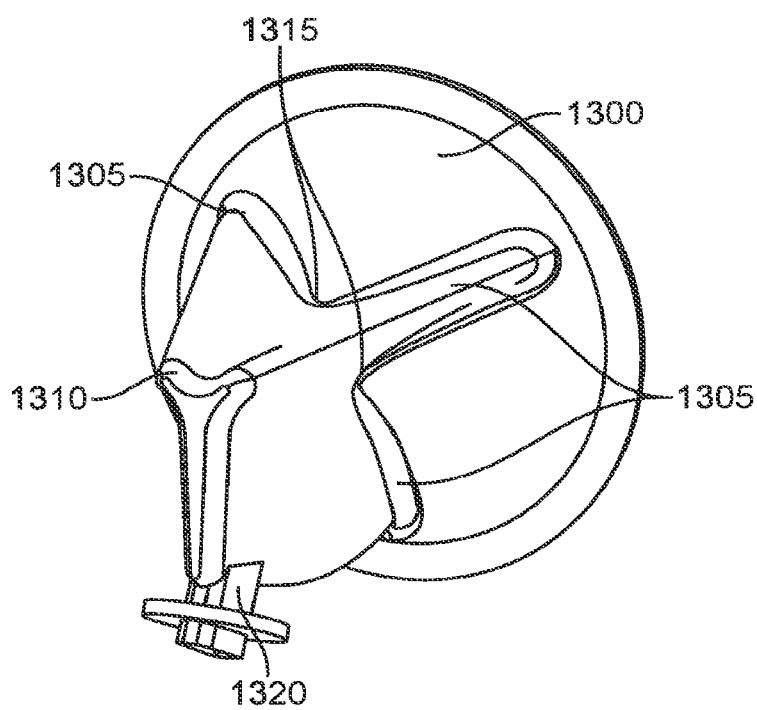

FIGS. 13A and 13B illustrate another exemplary embodiment of an expandable membrane 1300 having radial pleats 1305. FIG. 13A is a view from the side of the membrane engaging the breast, while FIG. 13B is a view from of the side of the membrane engaging the breast interface housing. The expandable membrane 1300 comprises three expandable pleats 1305 extending radially outward from the center of the expandable membrane. The expandable pleats can be distributed evenly about the circumference of the membrane, for example at about 120 degrees away from one another as shown. The pleats comprise valleys 1315 that are configured to expand radially outwards when vacuum pressure is applied at the expandable membrane by an actuatable assembly operatively coupled to the breast interface. The valleys are further configured to contract radially inwards when the breast interface returns to normal atmospheric pressure, or when positive pressure is applied at the membrane. The pleats converge at the apex 1310, which can be configured to remain in a substantially fixed position during actuation of the actuatable assembly. The expandable membrane further comprises a drain port 1320, wherein milk expressed from the breast by the movement of the expandable membrane can drain through the drain port 1320 into a collection vessel. The drain port 1320 can be disposed at the base of the apex 1310, such that the drain port can remain in a substantially fixed position longitudinally and radially during actuation of the actuatable assembly.

Figure 13C:
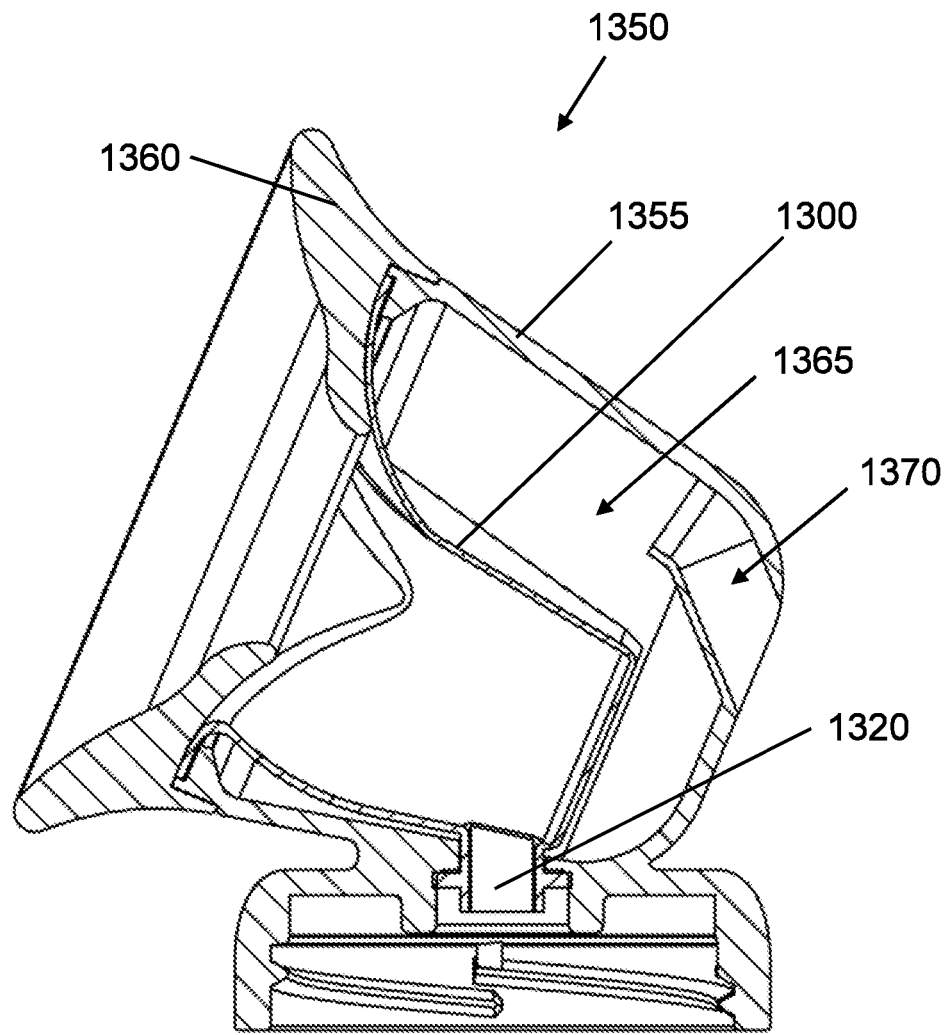
FIG. 13C is a cross-section of a breast interface comprising the expandable membrane illustrated in FIGS. 13A-13B.

FIG. 13C is a cross-section of a breast interface 1350 comprising the expandable membrane 1300 illustrated in FIGS. 13A-13B. The breast interface 1350 comprises a housing 1355, within which the expandable membrane 1300 is disposed. The breast interface further comprises a flange 1360 configured to engage and fluidly seal against the breast, the flange often comprising a resilient material that can conform to the breast. The housing 1355 comprises a fluid reservoir 1365 disposed between the housing and the expandable membrane, wherein fluid can be added to or removed from the fluid reservoir in order to move the expandable membrane and thereby generate pressure at the breast interface. The housing further comprises an outlet 1370 that can be coupled to a tube (not shown), wherein the tube is removably and operatively coupled to an actuatable assembly such as any of the pumps, pump mechanisms, or actuatable mechanisms disclosed herein. The fluid in the fluid reservoir 1365 can be hydraulically displaced by movement of the fluid in the tubing when the actuatable assembly coupled to the tubing is actuated. When fluid is removed from the fluid reservoir, a vacuum is generated at the breast interface, causing the pleats of the expandable membrane 1300 to expand radially outwards such that the membrane moves in a direction away from the breast, and thereby apply vacuum pressure at the breast. The vacuum pressure and the movement of the membrane can cause breast tissue to be pulled into the membrane, and milk to be expressed from the breast. When fluid is added to the fluid reservoir, the pleats contract radially inwards such that the expandable membrane moves in a direction towards the breast. The contraction of the pleats can return the breast interface to normal atmospheric pressure and allow the expressed milk to drain through the drain port 1320, or apply positive pressure at the breast to force the expressed milk out through the drain port. Upon release of the vacuum pressure, the breast tissue that had been pulled into the membrane can be released and/or compressed, thereby facilitating the expression of milk from the breast.

Milk Collection and Quantification System

With reference to FIG. 3, expressed milk drains through exit port 265 in flexible membrane 245 into a collection vessel 275. Collection vessel 275 can be any suitable container, such as a bottle or a bag. In many embodiments, collection vessel 275 is removably coupled to flexible membrane 245. Collection vessel 275 can be coupled directly or remotely via any suitable device such as extension tubing.

In many instances, it can be desirable to track various data related to milk expression and collection, such as the amount of milk production. Currently, the tracking of milk production is commonly accomplished by manual measurements and record-keeping. Exemplary embodiments of the device described herein may provide digital-based means to automatically measure and track milk production for improved convenience, efficiency, and accuracy.

Figure 9A:
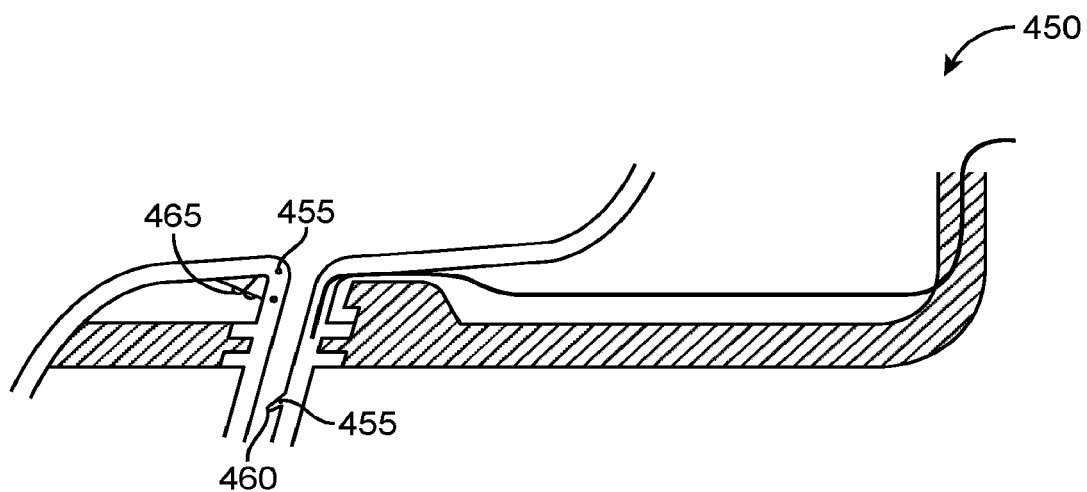
FIG. 9A is a cross-sectional view of an exemplary embodiment of integrated sensors within a breast interface.
Figure 9B:
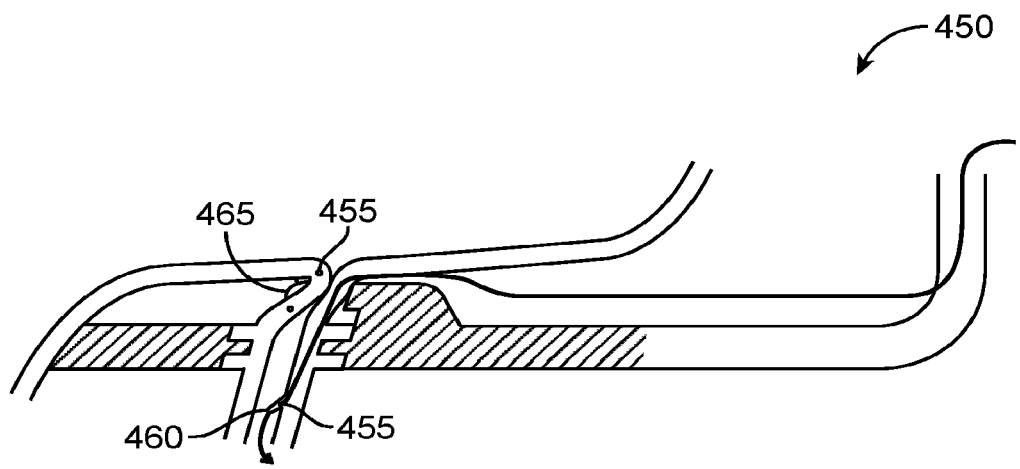
FIG. 9B is a cross-sectional view of another exemplary embodiment of integrated sensors within a breast interface.

FIGS. 9A and 9B illustrates exemplary embodiments of a breast interface 450 with one or more integrated sensors 455. Sensors 455 are preferably located in, near, or proximal to flap valve 460, but may also be located in, near, or proximal to exit valve 465 or other control mechanism used to control fluid flow, or in any other suitable location for detecting, measuring, or monitoring fluid flow. In a preferred embodiment, at least one sensor 455 can be integrated into a valve mechanism that is opened by fluid flow and can detect the length of time that the valve mechanism is opened. The sensor signal can be interrogated to quantify the fluid flow. Suitable sensors are known to those of skill in the art, such as accelerometers, Hall effect sensors, and photodiode/LED sensors. The breast interface can include any sensor that can detect, measure, or monitor fluid flow as known in the art or yet to be developed and can include a single sensor or multiple sensors to quantify milk production.

Figure 10:
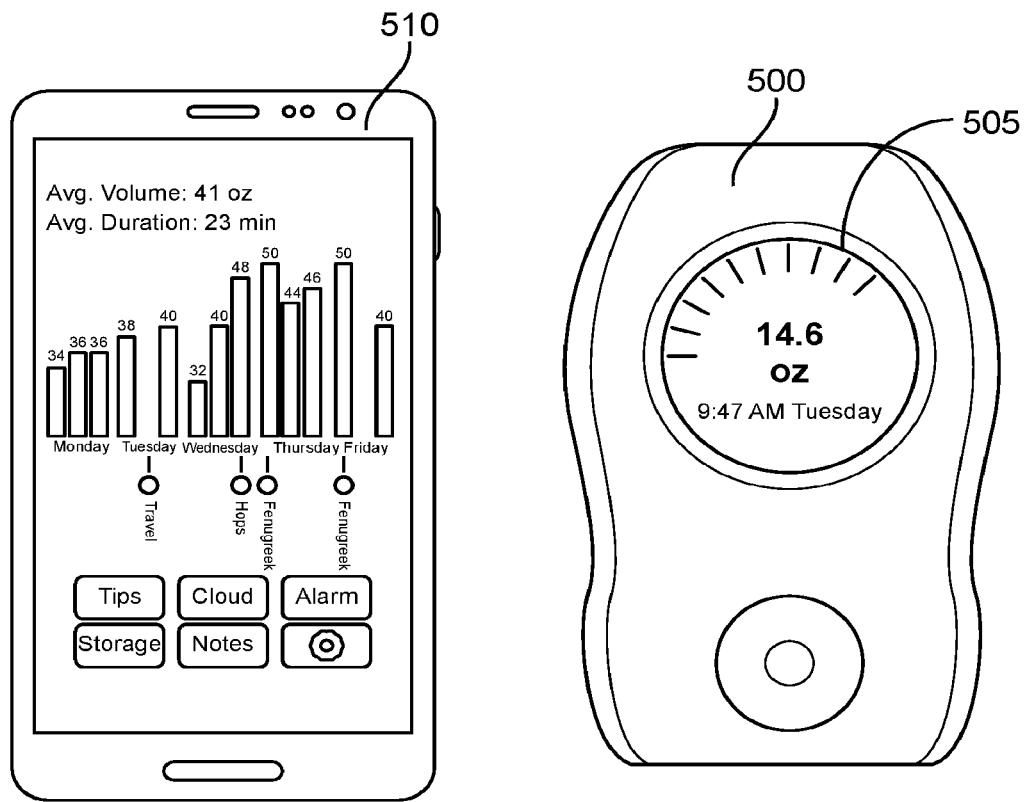
FIG. 10 illustrates an exemplary embodiment of a pendant unit and a mobile device.

FIG. 10 illustrates an exemplary embodiment of pendant unit 500 in which milk expression data is shown on a display screen 505. In many embodiments, the pendant unit 500 can collect, process, and store and display data related to milk expression. Preferably, the pendant unit 500 can transmit the data to a second device, such as a mobile phone 510.

Figure 11:
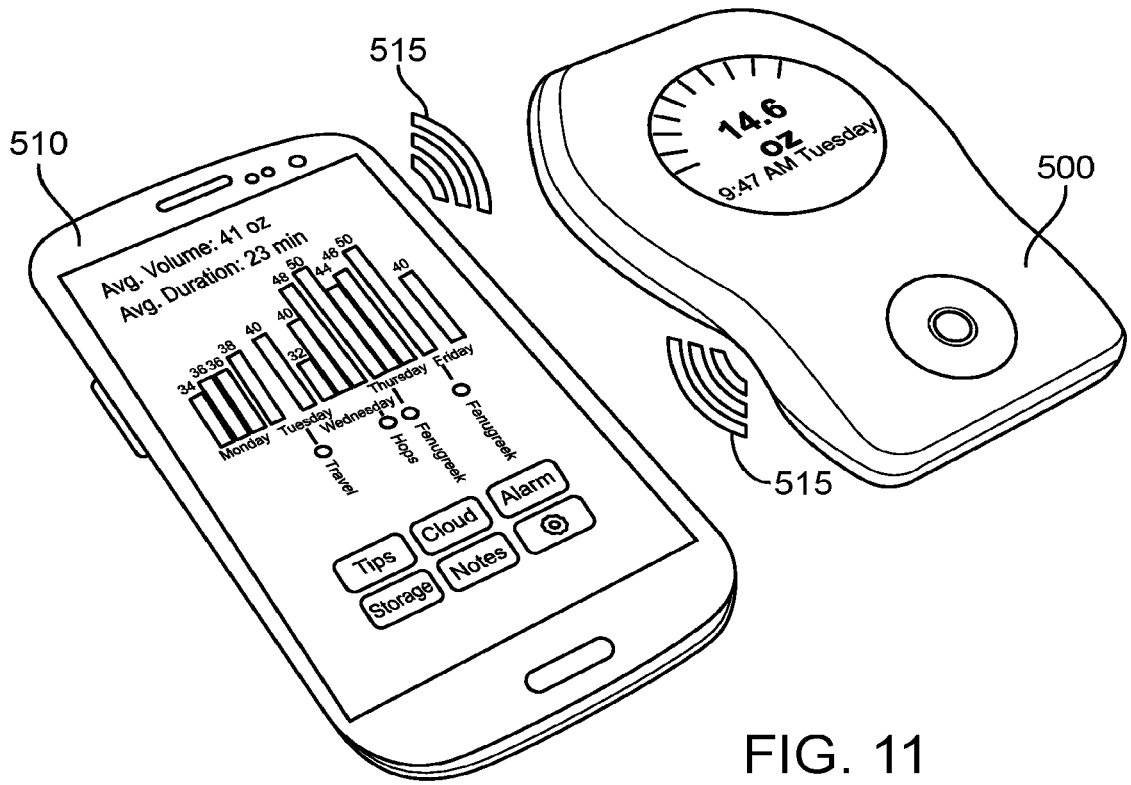
FIG. 11 illustrates an exemplary embodiment of a pendant unit in communication with a mobile device.

FIG. 11 illustrates data transmission 515 between pendant unit 500 and a mobile phone 510. Suitable methods for communication and data transmission between devices are known to those of skill in the art, such as Bluetooth or near field communication.

In exemplary embodiments, the pendant unit 500 communicates with a mobile phone 510 to transmit milk expression data, such as expression volume, duration, and date. The mobile phone 510 includes a mobile application comprising a processor to collect, process, and/or aggregate the expression data and to display it to a user in an interactive format. For example, as shown in FIGS. 10 and 11, a user interface can be provided to display data and other outputs generated by the processor that are related to milk expression. Data and other outputs related to milk expression can include, for example, the time milk was expressed, the duration of the expression of milk, and the volume and/or rate of milk expressed at any given time or duration of time. Similarly, the display of data and other outputs can include a visual representation of the volume and/or rate of milk expressed over a period of time to provide a user with an overview and/or a breakdown of milk expression over a given time period or periods. For example, as shown in FIGS. 10 and 11, a user may view a historical record of her milk expression over the period of one week, wherein the display can include the volume and/or rate of milk expressed for each day of the week. The user interface can provide buttons or icons that allow the user to interact and provide additional information to the processor. Preferably, the mobile application comprises additional features that allow the user to provide and overlay additional information such as lifestyle choices, diet, and strategies for increasing milk production, and any other additional information that might be used by the mobile application. Such information may be used, for example, in order to facilitate the comparison of such information with milk production statistics. The additional information may also be used in combination with the expression data by the mobile application to generate new information or outputs that can be informative to the user. As another example, the pendant unit 500 can send information about the times of pump usage to the mobile phone 510 so that the mobile application can identify when pumping has occurred and set reminders at desired pumping times. Such reminders can help avoid missed pumping sessions, and thus reduce the incidence of associated complications such as mastitis.

One of skill in the art will appreciate that components and features of any of the exemplary embodiments of the milk collection and quantification system can be combined or substituted with components and features of any of the embodiments of the present invention as described herein.

Posterior Compression at Breast Interface

Figure 16A:
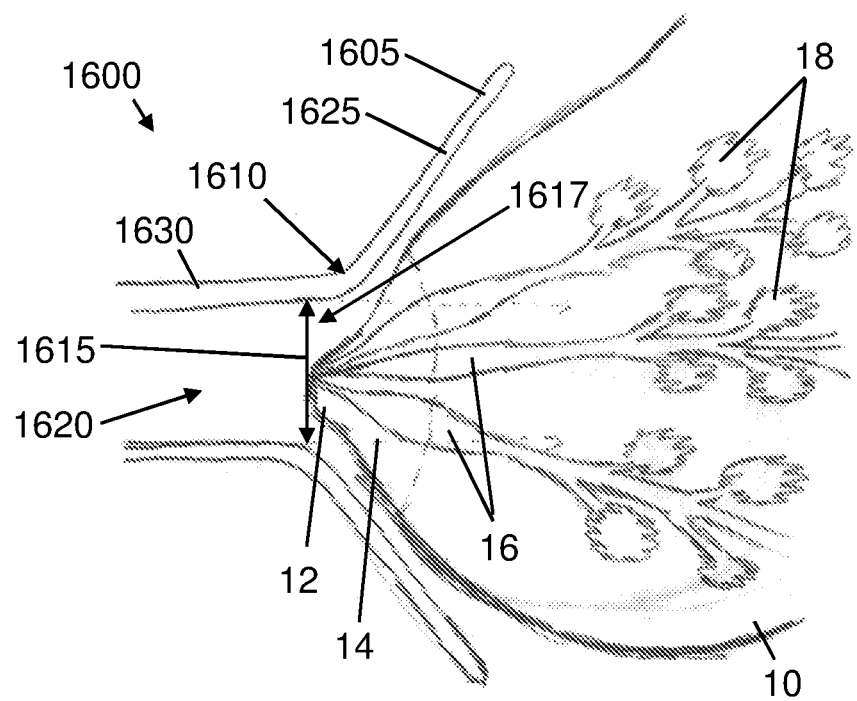
FIG. 16A shows a breast interface during the resting phase.
Figure 16B:
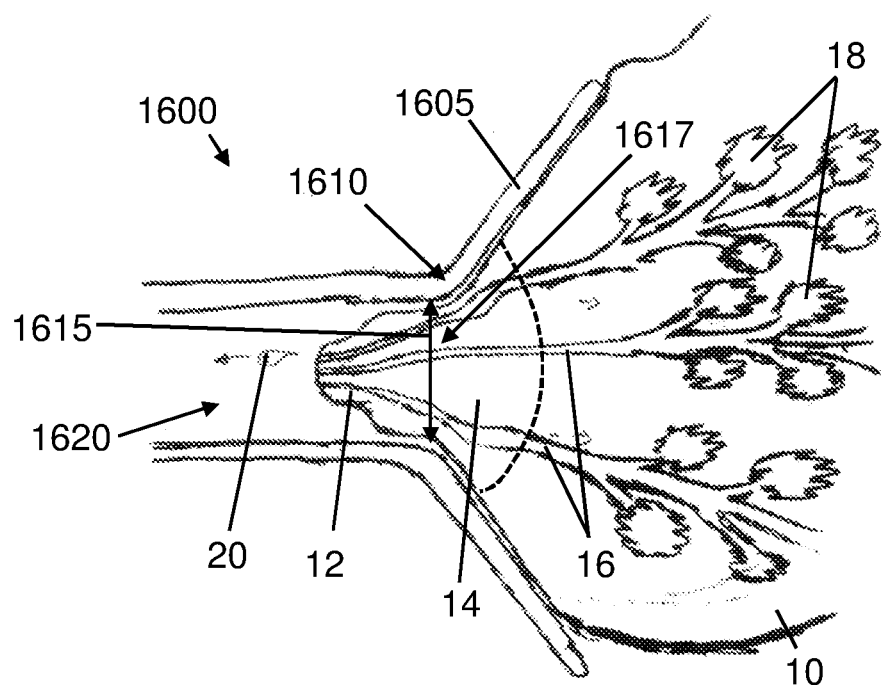
FIG. 16B shows the breast interface of FIG. 16A during the expression phase.
Figure 16C:
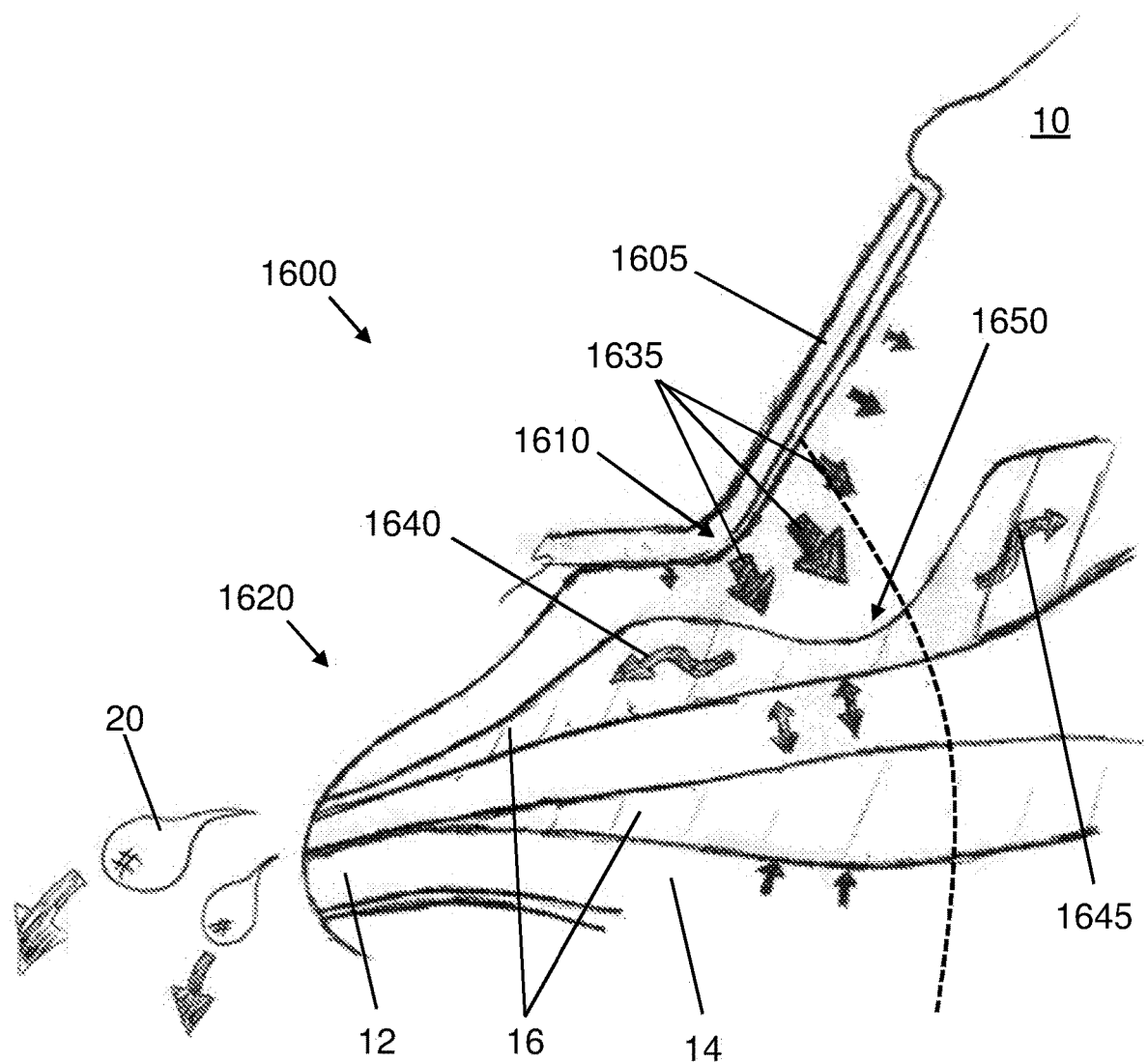
FIG. 16C is a detail view of the breast interface of FIG. 16B.

FIGS. 16A-16C illustrate forces applied at the breast interface during breast milk expression using a breast pump. FIG. 16A shows a breast interface 1600 during a resting phase, wherein no vacuum pressure is applied at the breast interface. FIG. 16B shows the breast interface 1600 during an expression phase, wherein vacuum pressure is applied at the breast interface. FIG. 16C is a detail view of FIG. 16B, schematically showing the forces generated at the breast interface 1600 during the expression phase. A breast interface 1600 of a breast milk expression device typically comprises a flange 1605, such as any flange as described herein, configured to engage a breast 10 and form a seal thereagainst during breast milk expression. The flange and/or the breast interface may comprise an elbow 1610, wherein the elbow comprises the transition zone between the portions of the flange configured to engage the breast tissue and the portions of the breast interface configured to provide the area into which breast milk is expressed. The elbow can define the internal width or diameter 1615 of the breast interface opening 1617 into the breast milk expression area 1620, into which portions of the breast are pulled during breast milk expression. For example, in the flange 1605 as shown in FIGS. 16A and 16B, wherein the flange comprises a frustoconical portion 1625 that engages the breast and a neck portion 1630 that provides the expression area 1620, the elbow 1610 may be disposed at or near the transition point between the frustoconical portion and neck portion. In a flange coupled to a housing and/or an expandable member disposed within the housing, as shown in FIGS. 3A-3B, 6-7, 12B, or 13C, the elbow may be disposed at or near the transition point between the flange and the housing and/or expandable member. As shown in FIG. 16B, during the expression phase, the nipple 12 and portions of the areola 14 may be positioned within the internal diameter 1615, and portions of the breast near the nipple and/or the areola may be compressed against portions of the breast interface near the elbow 1610. In response to this compressive force, portions of the breast interface near the elbow can apply localized counter forces 1635 at the anterior portions of the breast near the nipple and the areola. The counter forces in turn cause anterior compression 1650 of the milk ducts 16, which can cause milk 20 to flow in a first direction 1640 towards and out through the nipple 12, and/or in a second direction 1645 back towards the alveoli 18 of the mammary glands. The retrograde flow of the milk in the second direction can result in a decreased efficiency of breast milk expression.

Figure 17A:
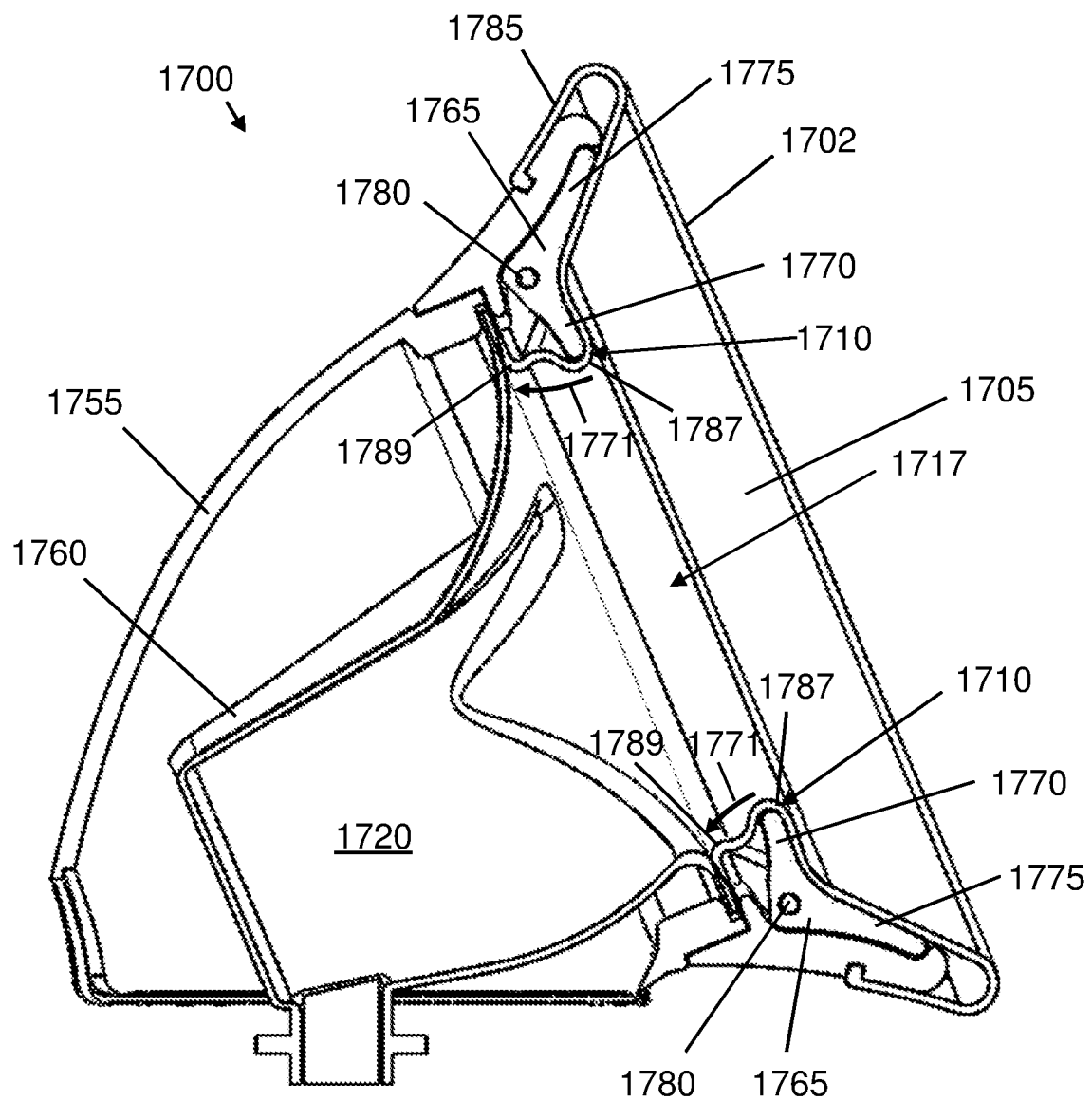
FIGS. 17A and 17B show side cross-sectional views of an exemplary breast interface comprising one or more levers.
Figure 17B:
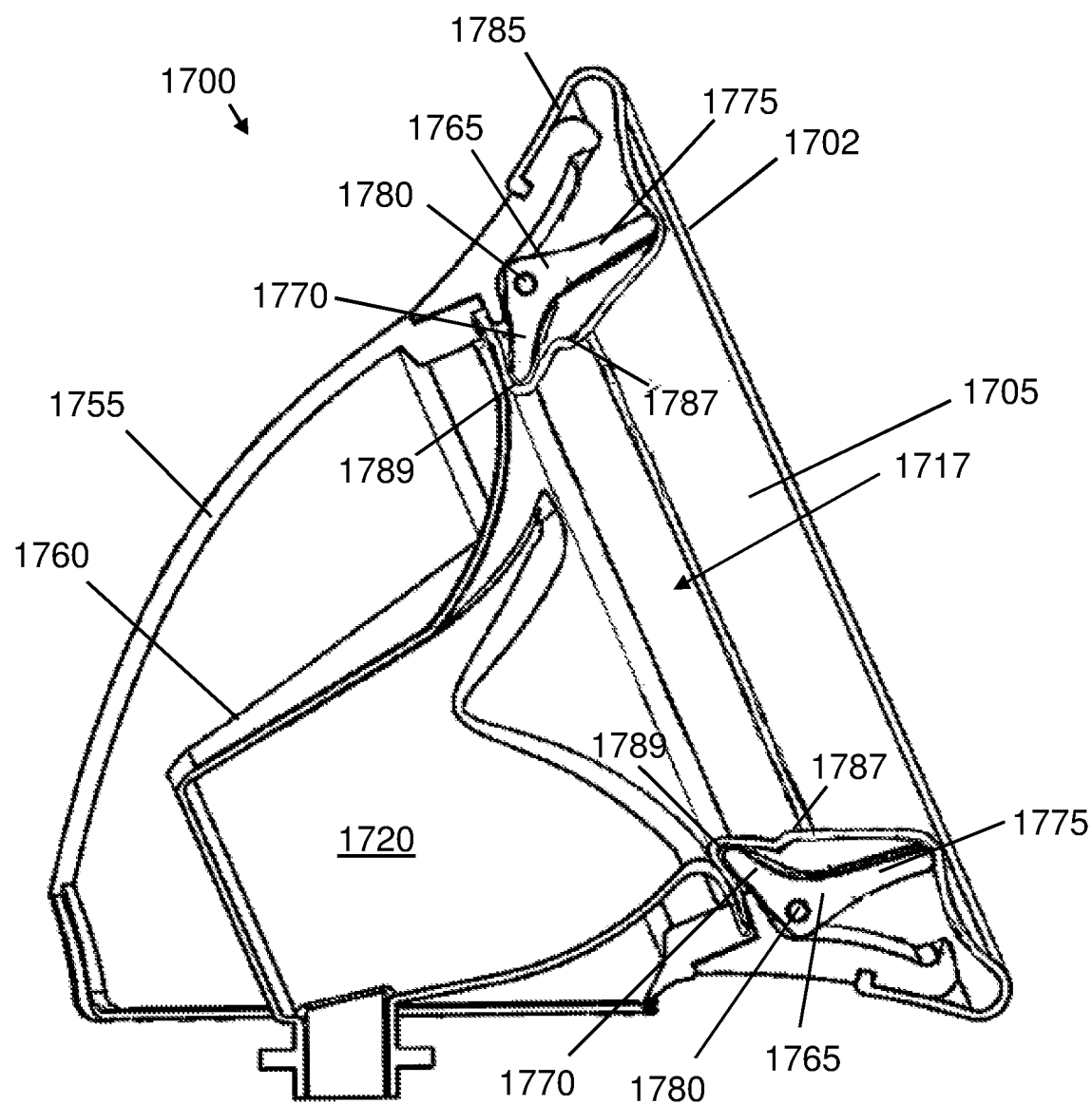
Figure 17C:
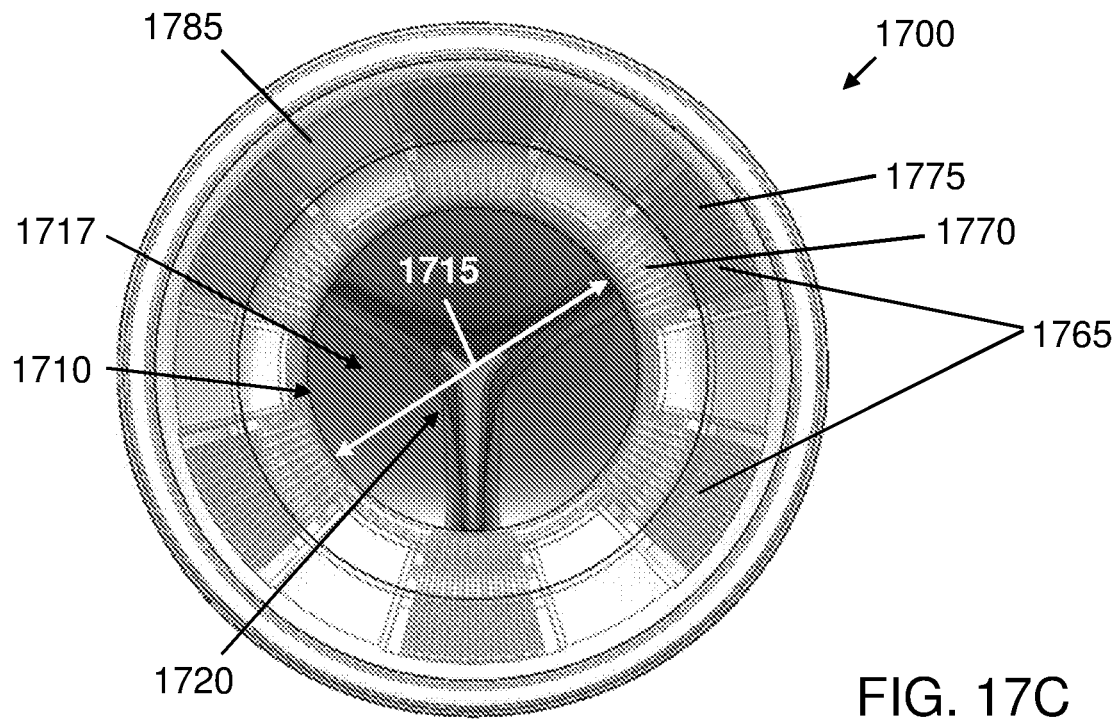
FIG. 17C shows a front view of the breast interface of FIGS. 17A-17B.
Figure 17D:
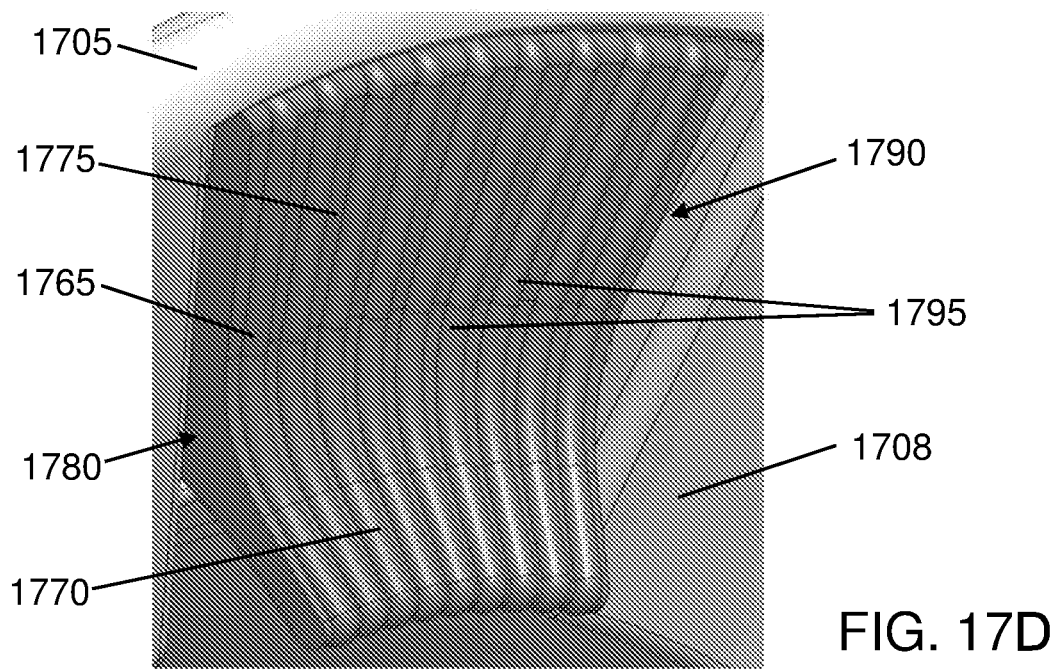
FIG. 17D is a detail view of a lever of FIGS. 17A-17B in the resting configuration.

FIGS. 17A-17D illustrate an exemplary embodiment of a mechanism to generate posterior compression at the breast interface. FIGS. 17A and 17B show side cross-sectional views of a breast interface 1700 comprising one or more actuatable elements such as levers 1765 disposed near the distal end 1702 of the breast interface. FIG. 17A shows the breast interface in the resting phase, wherein FIG. 17B shows the breast interface in the expression phase. FIG. 17C shows a front view of the breast interface 1700. FIG. 17D is a detail view of a lever 1765 in the resting configuration, during the resting phase. As shown in FIGS. 17A and 17B, the exemplary breast interface 1700 comprises a housing 1755, to which an expandable membrane 1760 and a flange 1705 are coupled. The housing, expandable membrane, and flange may be similar in many aspects to any housing, expandable membrane, or flange, respectively, described herein with respect to any embodiment of a breast interface. For example, the flange may comprise a resilient material configured to help engage and fluidly seal against the breast, and the housing may comprise a rigid shell within which the expandable membrane is disposed, wherein the expandable membrane is configured to move toward or away either radially and/or axially from the breast in response to actuation of an actuatable assembly operably coupled to the breast interface. The breast interface may further comprise the mechanism to generate posterior compression at the breast interface. In the embodiment of FIGS. 17A-17D, the posterior compression mechanism comprises one or more movable members such as one or more levers 1765 disposed near the distal end 1702 of the breast interface. Each lever 1765 may comprise a first arm 1770 and a second arm 1775 configured to rotate relative to one another about a pivot point 1780. The first arm may be disposed at an anterior portion of the lever, and the second arm disposed at a posterior portion of the lever, wherein the anterior portion is configured to engage an anterior portion of the breast and the posterior portion is configured to engage a posterior portion of the breast when the breast is fluidly sealed against the flange. The first arm and the second arm may be joined at the pivot point. The longitudinal axes of the first and second arms may be non-collinear, such that the lever is bent about the pivot point. In the resting phase, shown in FIG. 17A, the lever is in the resting configuration, with the first arm substantially free to rotate inwards towards the expression area 1720, in the direction shown by arrow 1771. In the resting configuration, the first arm may protrude radially inwards into the opening 1717 of the breast interface. The first arm of the lever can thus comprise the elbow 1710 of the breast interface, wherein the elbow defines the internal width or diameter 1715 of the opening 1717 into the expression area 1720 (as best seen in FIG. 17C). As described herein, the elbow can generate anterior compression of the breast during the expression phase. During the expression of milk, a portion of the breast is pulled into the expression area via the vacuum pressure applied by the actuatable assembly. The breast then contacts and pushes on the first arm, causing the first arm to rotate inwards about the pivot point towards the expression area. The rotation of the first arm in turn causes the rotation of the second arm about the pivot point in the same direction. FIG. 17B shows the breast interface 1700 during the expression phase, wherein the lever 1765 is in the expression configuration, with the second arm 1775 rotated radially inwards towards the opening 1717. The rotation of the second arm can apply a compressive force on a posterior portion of the breast engaged within the breast interface, as described in further detail herein. This posterior compression can complement and augment the anterior compression of the breast caused by the counter force generated near the elbow, to prevent retrograde flow of milk and thereby enhance expression of milk from the breast.

A breast interface may comprise any number of movable members, levers, or lever mechanisms arranged in any fashion near the distal end of the breast interface, such that the movable members, levers, or lever mechanisms may apply compressive force to posterior portions of the breast. For example, as shown in FIG. 17C, the breast interface may comprise six separate levers arranged radially symmetrically about the periphery of the flange. In another exemplary embodiment, the breast interface may comprise any number of levers arranged annularly about the flange either symmetrically or asymmetrically. In yet another exemplary embodiment, the breast interface may comprise a single movable member or lever that extends continuously about at least a portion of the periphery of the flange, or about the complete periphery of the flange.

In the embodiment shown in FIGS. 17A-17D, a plurality of levers can be integrated into the flange. As best seen in FIG. 17D, each lever 1765 may be disposed within a recessed region 1790 in the internal surface 1708 of the flange. Each lever may be coupled to the recessed region via the pivot point 1780, for example via a pin extending through the pivot point and through portions of the flange. In the resting configuration of the lever as shown in FIG. 17D, the front face of the second arm 1775 may be substantially aligned with the internal surface of the flange, while the back face may be substantially flush against the internal surface of the recessed region (as best seen in FIG. 17A). The first arm 1770 may be protruding radially inwards into the opening 1717 of the breast interface. When the breast interface comprises a plurality of levers distributed about the periphery of the flange, the plurality of first arms in the resting configuration may form an inner rim or lip 1777, as shown in FIG. 17B. When a breast is pulled into the breast interface, the breast can make contact with and push against this inner rim, causing rotation of the levers about the pivot point.

The flange and the levers may be enclosed within a cover 1785, as best seen in FIGS. 17A-17C. In the front view of FIG. 17C, the cover is shown in transparent form. The cover may comprise a soft, flexible material such as silicone, configured to allow the levers to rotate therein. The cover can facilitate sealing to the breast, while preventing pinching of the breast by any portion of the breast interface, such as the first arm and/or the second arm, during actuation of the actuatable assembly to elicit the vacuum phase and the return to the resting phase. The cover can comprise two pockets 1787 and 1789 configured to receive the end of the first arm 1770, wherein a first pocket 1787 receives the first arm in the resting configuration as shown in FIG. 17A, while the second pocket 1789 receives the first arm in the expression configuration as shown in FIG. 17B. To further facilitate rotation of the levers within the cover, the front face of the levers and/or the inner surface of the cover facing the levers may be provided with surface features configured to decrease friction between the two surfaces as the levers slide over the inner surface of the cover. For example, as shown in FIG. 17D, the front face of the levers may comprise vertical ribbing 1795, such as full fillet ribs, which can reduce friction by reducing the points of contact between the levers and the inner surface of cover. Optionally, the levers and the cover may be provided with corresponding surface features, such as interlocking vertical ribs, that can further facilitation slide with respect to one another during rotation of the levers.

Figures 18A, 18B:
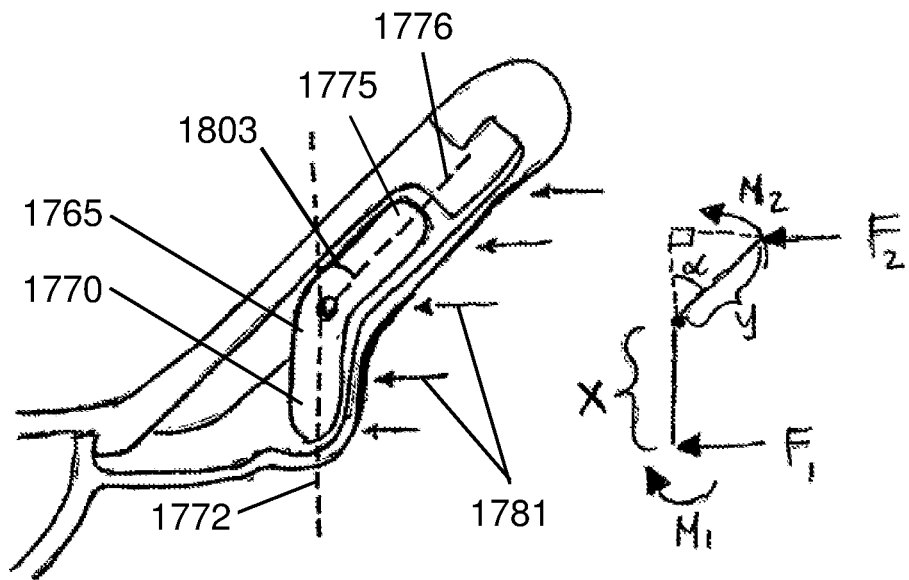
FIG. 18A schematically illustrates the forces applied to a lever during the expression phase.
FIG. 18B is a free-body diagram of the lever of FIG. 18A during the expression phase.
Figures 18C, 18D:
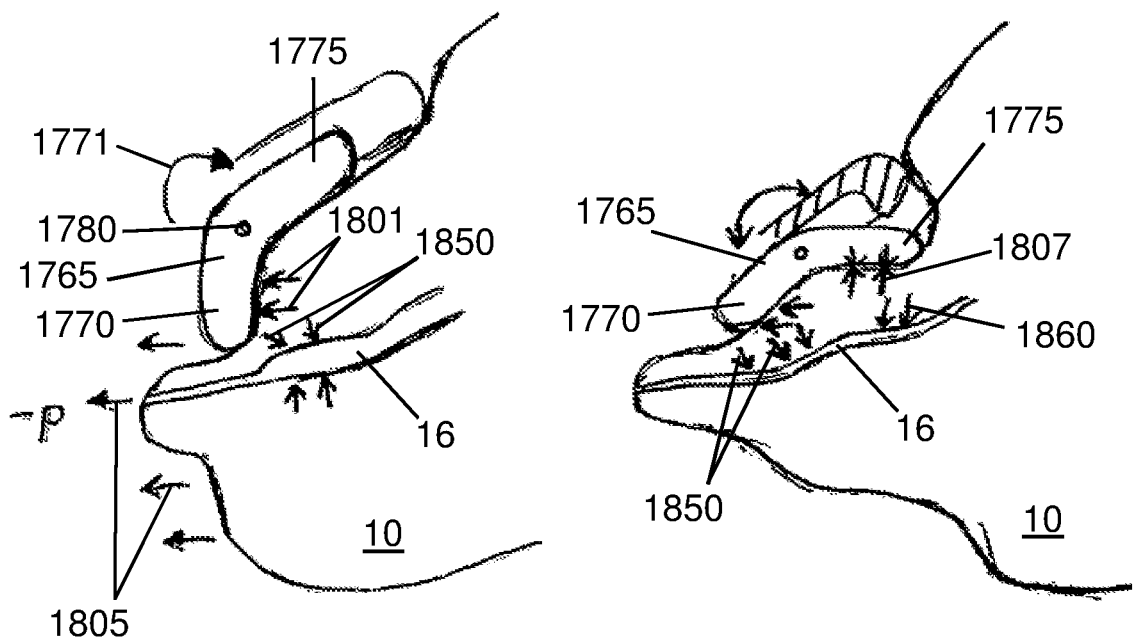
FIGS. 18C and 18D schematically illustrate a breast compressed against the lever of FIG. 18A.

FIG. 18A schematically illustrates the forces applied to a posterior compression lever 1765 as described herein during the expression phase. The lever 1765 may be designed such that, during the resting phase wherein minimal or no force is applied to the lever by the breast, the moment $M_2$ about the second arm 1775 in a second direction (shown as counter-clockwise in FIG. 18B) is greater than the moment $M_1$ about the first arm 1770 in a first direction opposite the second direction (shown as clockwise in FIG. 18B), such that the lever is disposed in the resting configuration as shown in FIG. 18A. For example, the cover placed over the lever may be configured to apply a greater horizontal force against the second arm than against the first arm, such that during the resting phase, absent significant horizontal force applied by the breast, the moment $M_2$ about the second arm in the second direction is greater than the moment $M_1$ about the first arm in the first direction. Alternatively or in combination, the lever may comprise an integrated spring element (e.g., a torsion spring disposed at the pivot point), configured to generate a greater moment about the second arm than about the first arm during the resting phase. The lever may be further designed such that when vacuum pressure is applied at the breast interface, the anterior compression of the breast against the first arm generates a moment about the first arm 1770 in the first direction that is greater than the moment about the second arm 1775 in the second direction. When vacuum is applied at the breast interface, the breast is compressed against the lever and exerts the horizontal force 1781. The horizontal force applied to the lever by the breast may be assumed to be substantially uniform across the surface of the lever. Therefore, in order to configure the lever to experience a greater moment about the first arm than about the second arm during the expression phase, an offset angle 1803 may be introduced between the first arm axis 1772 and the second arm axis 1776. Alternatively or in combination, the length of each arm may be adjusted to create the desired moment difference. FIG. 18B is a free-body diagram of the lever 1765 of FIG. 18A during the expression phase. The moment $M_1$ about the first arm in the first direction can be represented by $M_1=F_1 x$, whereas the moment $M_2$ about the second arm in the second direction opposite the first direction can be represented by $M_2=F_2 \cdot y \cdot \cos(\alpha)$, wherein $F_1$ is the horizontal force applied to the first arm by the breast, $F_2$ is the horizontal force applied to the second arm by the breast, x is the length of the first arm, y is the length of the second arm, and a is the offset angle between the axes of the first arm and the second arm. During the expression phase, assuming that $F_1=F_2$ and x=y, $M_1>M_2$, such that the lever moves from the resting configuration to the expression configuration FIGS. 18C and 18D schematically illustrate a breast 10 compressed against a posterior compression lever 1765 as described herein during the expression phase. FIG. 18C shows the beginning of the expression phase, while FIG. 18D shows the end of the expression phase. At the beginning of the expression phase, vacuum pressure 1805 is pulls the breast into the expression area of the breast interface, and in turn the breast applies horizontal force 1801 against the first arm of the lever. The first arm, which can comprise the elbow of the breast interface, in turn applies a localized counter force against the breast, resulting in the anterior compression 1850 of the milk ducts 16 at the anterior portions of the breast. As discussed in reference to FIGS. 18A and 18B, the horizontal force 1801 generates a greater moment about the first arm 1770 in the first direction than about the second arm 1775 in the second direction, and the difference between the moments can cause the lever to rotate about the pivot point 1780 in the direction of the moment $M_1$, shown by arrow 1771. As shown in FIG. 18D, the rotation of the lever can cause the second arm to compress portions of the breast posterior to the anterior portions compressed against the first arm, in turn causing posterior compression 1860 of the milk ducts 16. The lever may continue to rotate until the reactive force 1807 from the breast on the second arm becomes sufficient to generate a moment $M_2$ about the second arm in the second direction that equals the moment $M_1$ about the first arm in the first direction. Upon release of vacuum pressure from the breast interface, the breast returns to its natural position, such that the horizontal force applied to the lever by the breast is relieved or minimized. Accordingly, the moment about the second arm in the second direction becomes greater than the moment about the first arm in the first direction, and the lever returns to its resting configuration, as shown in FIG. 18A.

Figure 19A:
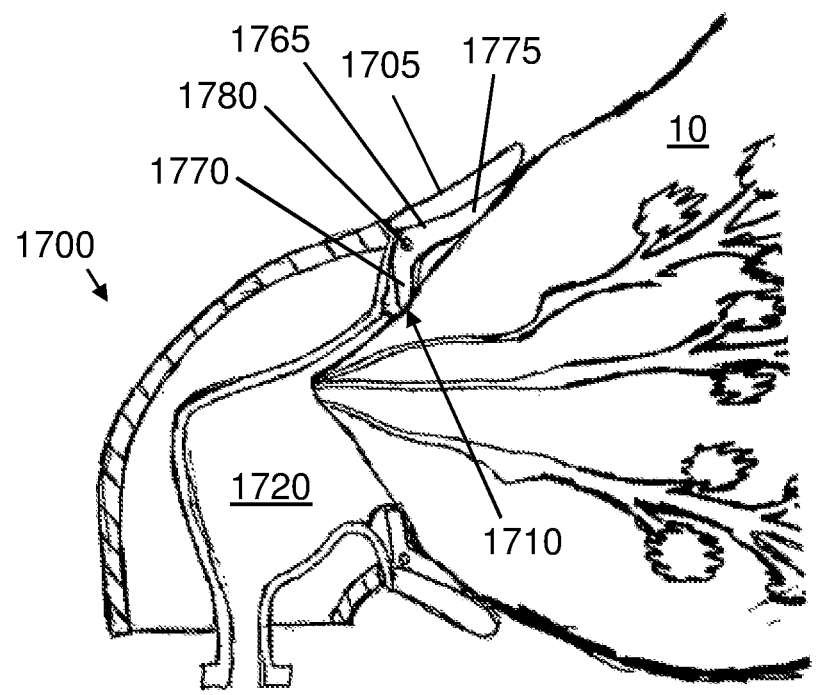
FIGS. 19A-19C show the breast interface of FIGS. 17A-17D with a breast received therein, during various phases of breast milk expression.
Figure 19B:
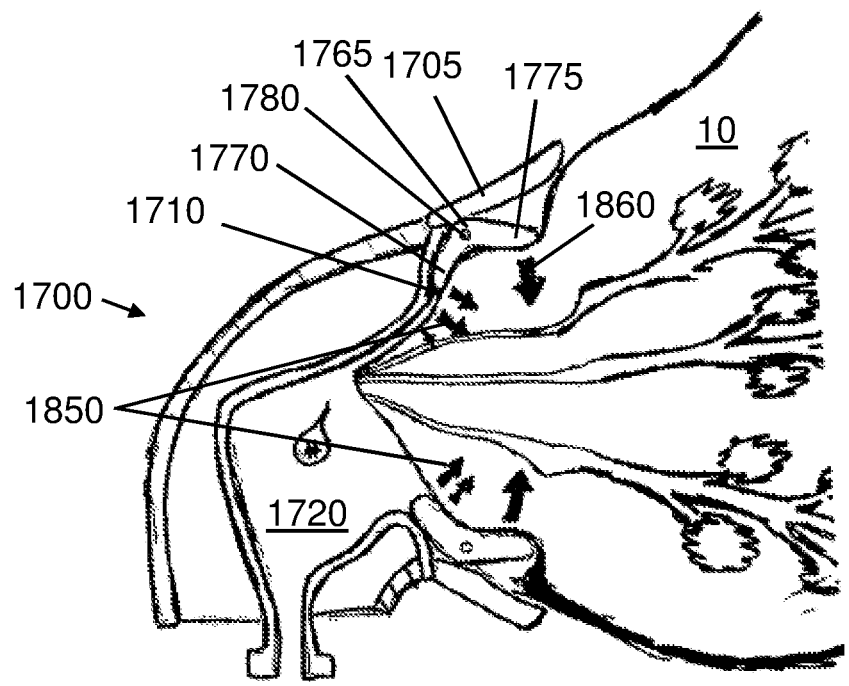
Figure 19C:
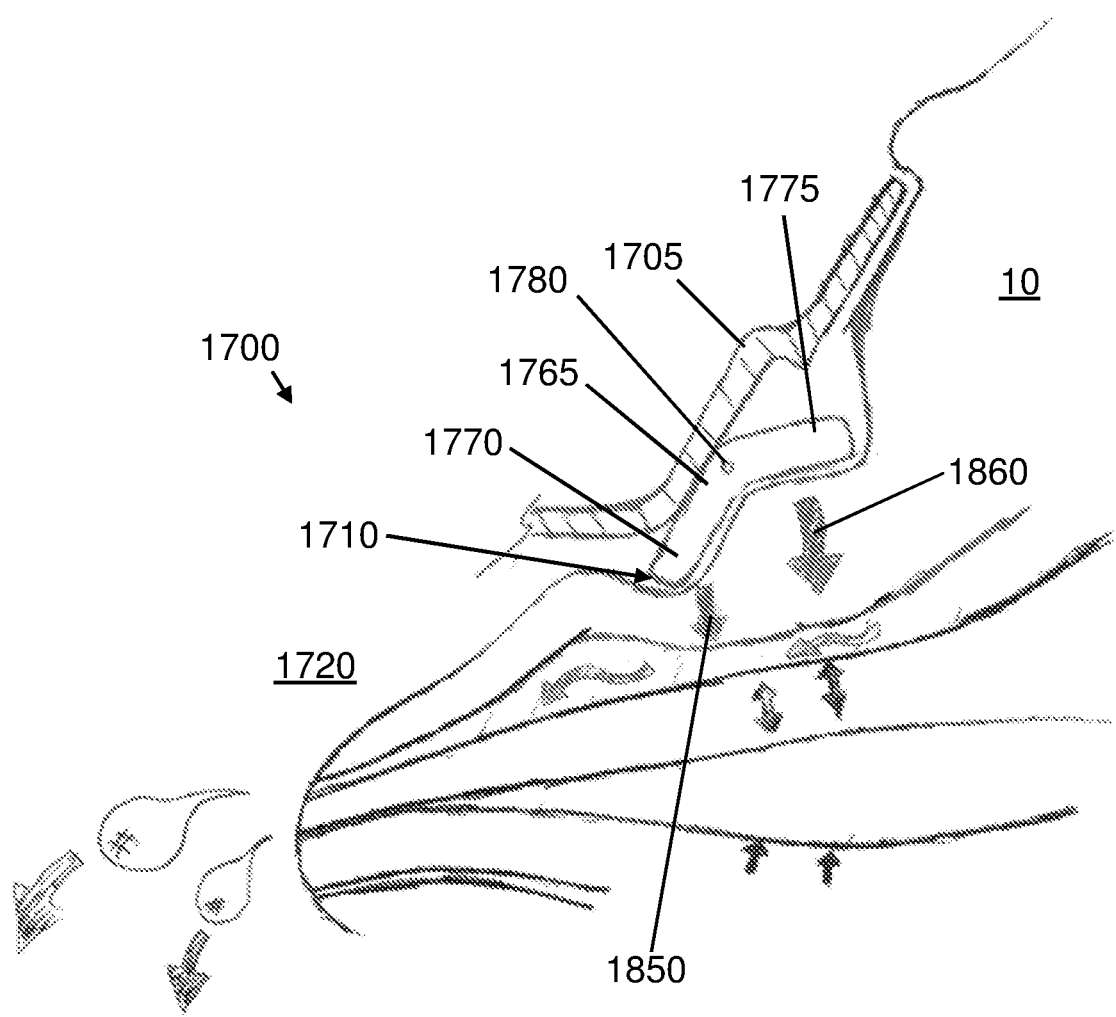

FIGS. 19A-19C show the breast interface of FIGS. 17A-17D with a breast received therein, during various phases of breast milk expression. FIG. 19A shows the breast 10 received in the breast interface 1700 during the resting phase (e.g., prior to the beginning of pump session, between actuation cycles of the actuatable assembly, or after completion of pump session). In this phase, no vacuum pressure is applied at the breast interface, and the breast is in its resting position, engaged into and/or sealed against the flange 1705, but not actively compressing against the lever 1765. Accordingly, the lever is also in the resting configuration, wherein the first arm 1770 is free to rotate inwards towards the opening into the expression area 1720. FIG. 19B shows the breast received in the breast interface during the expression phase. FIG. 19C is a detail view of FIG. 19B, schematically showing the forces generated at the breast interface during the expression phase. During the expression phase, the breast is first pulled into the breast interface by the vacuum pressure generated by the actuatable assembly coupled to the breast interface. As the breast is pulled in, it compresses against the first arm 1770 of the lever comprising the elbow 1710 of the breast interface, thereby generating localized counter forces near the elbow that cause anterior compression 1850 of anterior portions of the breast tissue. Upon compression of the breast against the first arm of the lever, the lever rotates about the pivot point 1780 to transition into the expression configuration shown in FIGS. 19B and 19C. In the expression configuration, the second arm 1775 of the lever applies posterior compression 1860 at posterior portions of the breast tissue. Upon release of vacuum pressure from the breast interface, the breast returns to its natural position, and the levers also return to their resting configuration, as shown in FIG. 19A. Thus, upon application of vacuum pressure at the breast interface, the levers generate both anterior compression and posterior compression that are closely coupled temporally, with anterior compression quickly followed by posterior compression.

The posterior compression of the breast can apply additional compression on posterior portions of the milk ducts after the anterior compression has pushed some milk out of the ducts. This additional compression can not only help prevent some retrograde flow of milk back towards the alveoli of the mammary glands, but also help express more hind milk. In addition to the helping to improve expression efficiency, a mechanism as described herein for providing posterior compression of the breast can also mimic the peristaltic motion of a nursing baby's jaws, lips, and/or tongue, thus providing a more comfortable experience for the user during pumping.

The specific configuration of the levers shown in FIGS. 17A-17D is provided by way of example only, and the movable members, levers, or lever mechanisms may be provided in any configuration suitable for applying posterior compression at posterior portions of the breast, with respect to the anterior portions of the breast compressed by the elbow feature. In particular, the configuration of the movable members, levers, or lever mechanisms may be modified to adjust the location at which the posterior compression is applied. For example, it may be desirable to move the location of application of posterior compression closer to the expression area to better accommodate breasts with smaller nipples/areolas, or it may be desirable to move the location of application of posterior compression closer to the distal end of the breast interface to better accommodate breasts with larger nipples/areolas. The configuration of the movable members, levers, or lever mechanisms may be modified in one or more of many ways to adjust the location at which the posterior compression is applied. For example, the pivot point of the levers may be moved closer to or farther from the expression area, the lengths of the first arm and/or the second arm may be shortened or lengthened, or the angle between the first arm and the second arm may be increased or decreased. The length of the second arm may be lengthened relative to the first arm in order to lengthen the distance between the anterior portion of the breast that is compressed by the first arm and the posterior portion of the breast that is compressed by the second arm.

Figure 20A:
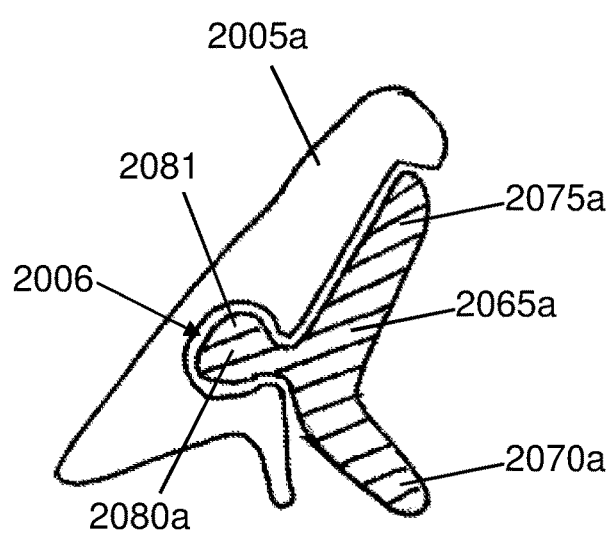
FIGS. 20A and 20B show other exemplary embodiments of a pivoting mechanism for a lever.
Figure 20B:
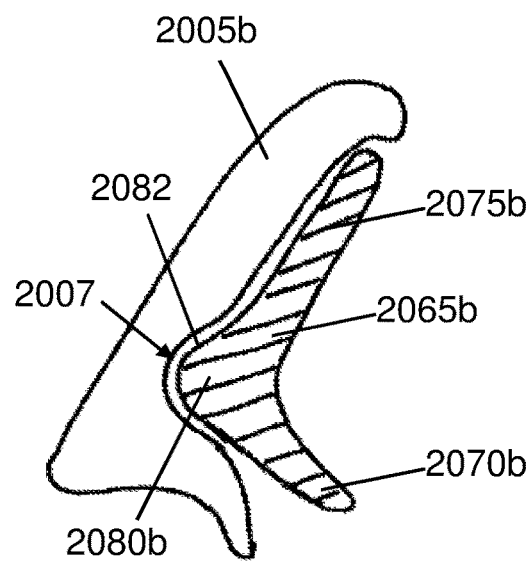

One or more movable members, levers, or lever mechanisms as described herein may be configured in one or more of many ways to rotate about a pivot point. For example, as described with references to the embodiment of FIGS. 17A-17D, the movable members, levers, or lever mechanisms may be coupled to the breast interface via a pin that extends through the pivot point, such that the lever can rotate about the pin. FIGS. 20A and 20B show other exemplary embodiments of a pivoting mechanism for a lever. In the embodiment of FIG. 20A, the lever 2065a comprises a rounded protrusion 2081 positioned near the transition zone between the first arm 2070a and the second arm 2075a. The rounded protrusion 2081 is embedded within a corresponding rounded slot 2006 of the flange 2005a, such that the rounded protrusion can rotate within the rounded slot to allow the first arm and the second arm to rotate about the pivot point 2080a. In the embodiment of FIG. 20B, the lever 2065b comprises a rounded shoulder 2082 positioned near the transition zone between the first arm 2070b and the second arm 2075b. The rounded shoulder 2082 engages a corresponding rounded indentation 2007 of the flange 2005b, such that the rounded shoulder can rotate against the rounded indentation to allow the first arm and the second arm to rotate about the pivot point 2080b. In either embodiment, a cover as described in reference to FIGS. 17A-17D may be disposed over the surfaces of the flange and the lever, in order to further secure the coupling between the lever and the flange. The lever-integrated pivoting mechanisms as shown in FIGS. 20A and 20B may be well-suited for incorporation into embodiments of a breast interface comprising a single lever extending continuously about the periphery of the flange. In such embodiments, the lever or a portion thereof (e.g., an integrated pin such as a rounded protrusion or a rounded shoulder) may comprise a material with some flexibility, to accommodate the transition between resting and expression configurations of the lever.

Optionally, the movable members, levers, or lever mechanisms may be removable from the breast interface. For example, the breast interface may comprise one or more levers with an integrated pin (e.g., rounded protrusion as shown in FIG. 20A), wherein the integrated pin can be removably snap-fitted into a corresponding slot of the flange. Alternatively or in combination, the breast interface may comprise a cover as described herein that is configured to removably fit over the removable lever and the flange. Removable levers may be provided in different sizes and/or shapes to accommodate different breast or nipple sizes.

FIG. 23 illustrates another exemplary embodiment of a posterior compression mechanism. The posterior compression mechanism of FIG. 23 may be similar in many aspects to the posterior compression mechanism shown and described in reference to FIGS. 17A-17D. For example, the breast interface 2300 may comprise a housing 2355, to which an expandable membrane 2360 and a flange 2305 are coupled. The housing 2355 may be similar in many aspects to the housing 1755, and the flange 2305 may be similar in many aspects to the flange 1705 of FIGS. 17A-17D. The breast interface 2300 may further comprise one or more movable members or levers 2365, which may be substantially similar to the levers 1765 of FIGS. 17A-17D. The expandable membrane 2360 may comprise an expandable portion 2362 and a flexible cover portion 2364, wherein the expandable portion is disposed within the housing and configured to expand in response to actuation of the actuation mechanism operably coupled with the breast interface, and the flexible cover portion is disposed over the levers. The expandable portion 2362 may be similar in many aspects to expandable portions of membranes as described herein with reference to various embodiments. For example, the expandable portion may comprise a plurality of radial pleats configured to enable expansion and contraction of the membrane about the nipple during milk expression. The flexible cover portion 2364 may be similar in many aspects to the cover 1785 of FIGS. 17A-17D. For example, the flexible cover portion may comprise pockets 2387 and 2389 each configured to receive a first arm end of a lever 2365 in the resting configuration and in the expression configuration, respectively, as described with reference to FIGS. 17A-17B.

While the lever mechanism of FIGS. 17A-17D is shown and described with respect to an embodiment of a breast interface comprising an expandable membrane, the lever mechanism may be incorporated into any embodiment of a breast interface. For example, the lever mechanism may be incorporated into an embodiment of a breast interface comprising a funnel-shaped flange as shown in FIGS. 16A-16B. One or more movable members, levers, or lever mechanisms substantially as described herein may be coupled to an interior surface of any breast interface and/or flange, such that the one or more movable members, levers, or lever mechanisms can apply posterior compression on the milk ducts as described herein.

Figure 21A:
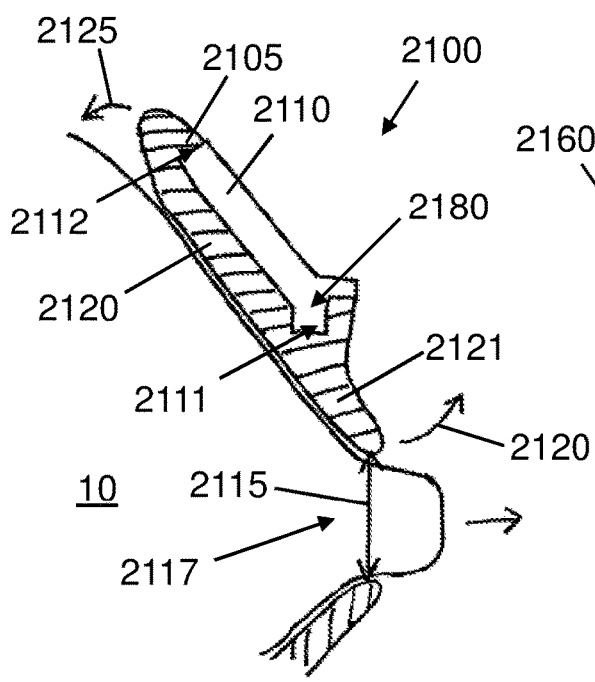
FIGS. 21A and 21B illustrate another exemplary mechanism for creating posterior compression of the breast during milk expression.
Figure 21B:
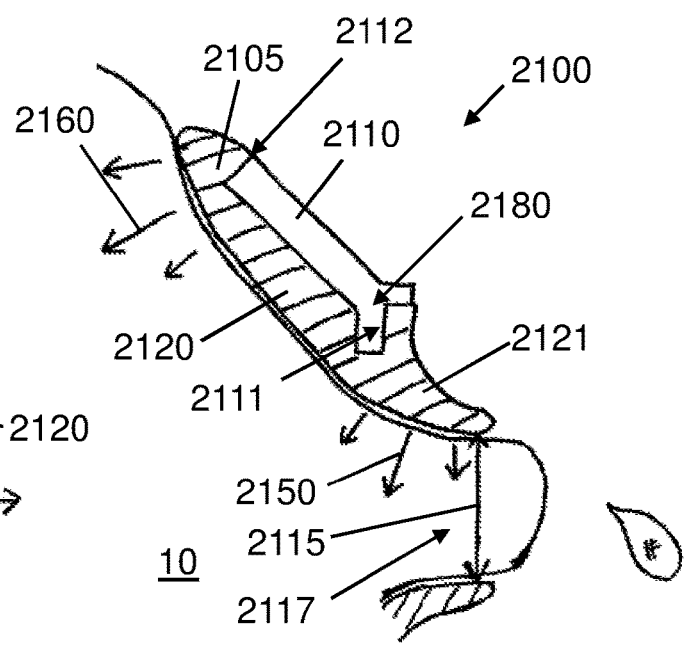

FIGS. 21A-21B illustrate another exemplary embodiment of a posterior compression mechanism. The breast interface 2100 may comprise a flange 2105 having a movable member comprising a substantially rigid member 2110 coupled to a flexible member 2120. As shown, the substantially rigid member may be embedded within the flexible member, extending from a anterior or proximal portion 2111 to a posterior or distal portion 2112. The flexible member may extend along the complete length and past the anterior or proximal end of the substantially rigid member. The anterior portion 2121 of the flexible member, extending past the anterior end of the rigid member, may be free to bend under pressure about a pivot point 2180, disposed near the anterior portion of the substantially rigid member. FIG. 21A shows the breast interface at the beginning of a vacuum phase. When vacuum pressure is applied at the breast interface and the breast 10 is pulled into the breast interface, the breast can compress against the anterior portion 2121 of the flexible member, causing the anterior portion to bend in the direction shown by arrow 2120. This bending of the anterior portion can in turn cause the substantially rigid member to rotate about the pivot point in the direction shown by arrow 2125. FIG. 21B shows the breast interface at the end of the vacuum phase. In this phase, the anterior portion 2121 of the flexible member 2120 is bent inwards towards the expression area, such that the internal diameter or width 2115 of the breast interface opening 2117 is increased compared to the initial diameter 2115 before the bending of the flexible member (shown in FIG. 21A). In addition, the rigid member is rotated downwards into the breast 10. In this configuration, the anterior portion of the flexible member and/or the anterior portion of the substantially rigid member apply anterior compression 2150 to the breast, while the posterior portion 2112 of the rigid member applies posterior compression 2160 to the breast. Thus, in this embodiment, a portion of the flange itself acts as a movable member or lever to apply temporally coupled anterior and posterior compression to the breast during the application of vacuum pressure at the breast interface.

Figure 24:
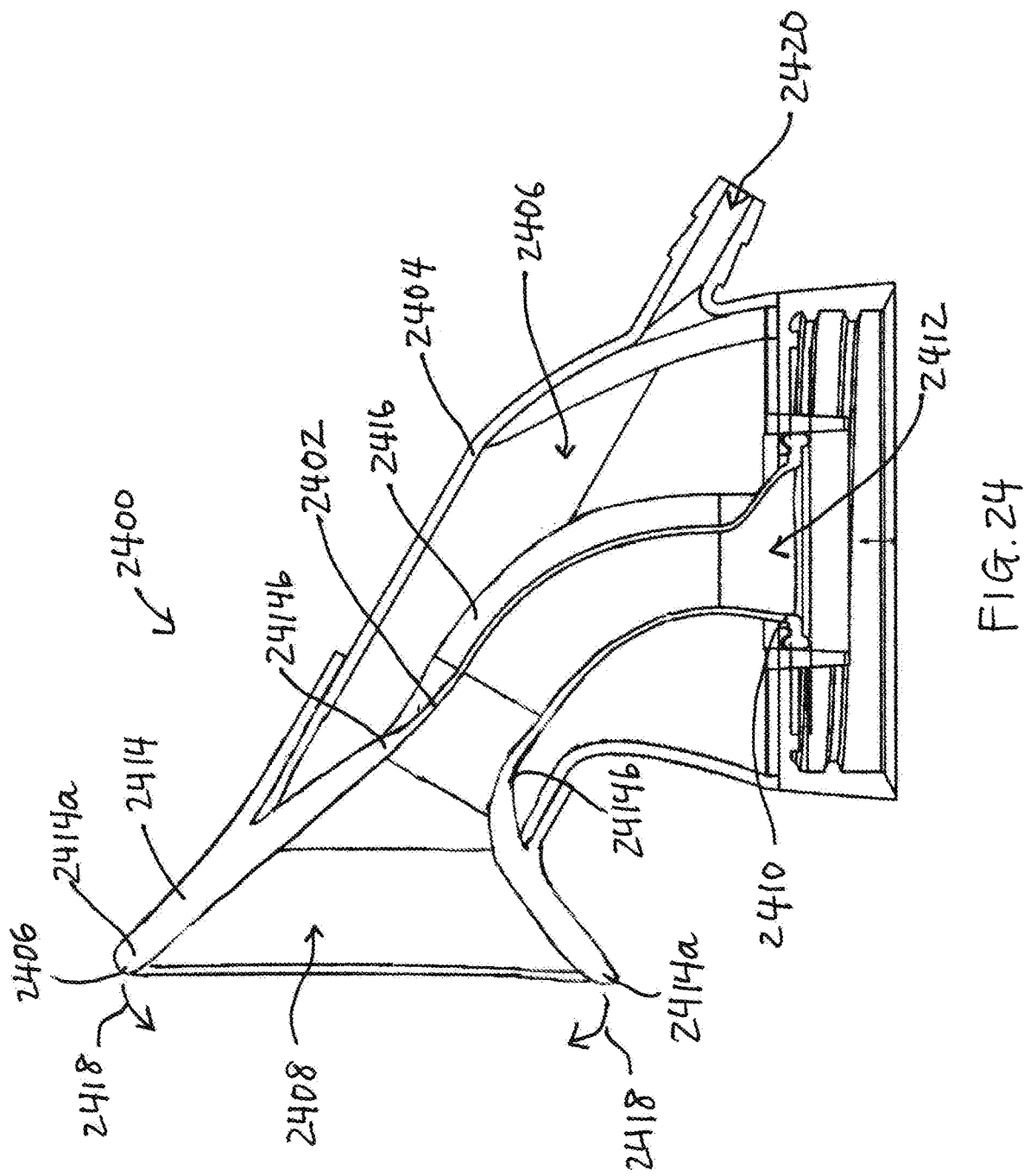
FIG. 24 illustrates an exemplary embodiment of a breast interface comprising a posterior compression mechanism integrated with an expandable membrane.

FIG. 24 illustrates an exemplary embodiment of a breast interface comprising a posterior compression mechanism integrated with an expandable membrane. The breast interface 2400 comprises an expandable membrane 2402 coupled to a rigid housing 2404 to form a reservoir 2406 therebetween, as described with reference to various embodiments herein. The expandable membrane comprises a first end 2406 defining a first opening 2408 configured to receive at least a nipple of a breast therethrough, and a second end 2410 defining a second opening 2412 configured to allow expressed breast milk to drain therethrough. The expandable membrane 2402 comprises a flange portion 2414 and an expandable portion 2416. The expandable portion 2416 is disposed within the housing and configured to expand radially toward and away from a nipple inserted into breast interface through the first opening, as described herein in reference to various embodiments. The expandable portion may, for example, comprise a plurality of radial pleats, as described herein. The flange portion 2414 may extend distally past the housing, and have a thickness that is greater than the thickness of the membrane at the expandable portion. The thicker flange portion can accordingly have a greater rigidity compared to the thinner expandable portion, allowing the rigid flange portion to function as the movable member of the flange in a manner similar to the levers 1765 or the rigid member 2110 as shown and described in reference to FIGS. 17A-17D and 21A-21B, respectively. For example, when vacuum pressure is applied at the breast interface via movement of fluid out of the reservoir 2406 (e.g., through the fluid port 2420), the expandable portion 2416 of the expandable membrane expands and moves away from the breast. Consequently, the breast is pulled axially into the breast interface, such that an anterior portion of the breast compresses against the anterior portion 2414b of the substantially rigid flange portion (anterior compression). The movement of anterior portion 2414b away from the nipple and towards the housing can in turn cause the posterior portion 2414a of the substantially rigid flange portion to rotate about a pivot point disposed near the anterior portion 2414b of the rigid flange portion. The posterior portion 2414a can consequently move in the direction shown by the arrow 2418, towards and into the breast at a posterior portion of the breast (posterior compression). The application of posterior compression following anterior compression can help improve the efficiency of milk expression by preventing the retrograde flow of milk, as described herein.

Figure 22A:
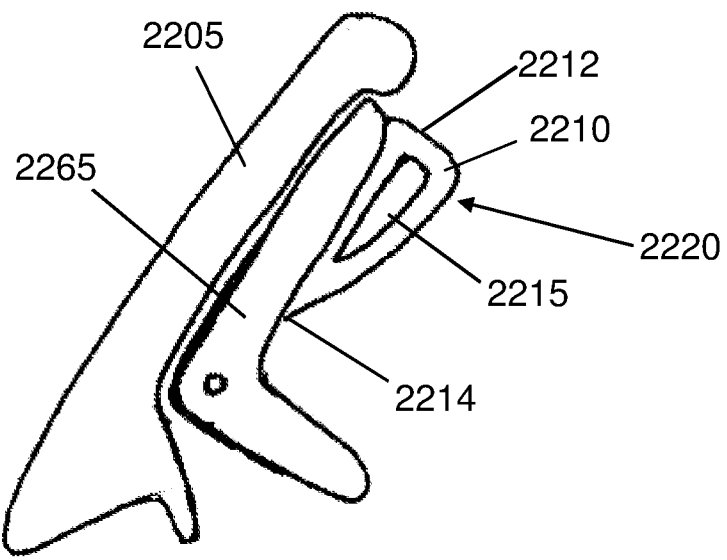
FIGS. 22A and 22B illustrate another exemplary mechanism for creating posterior compression of the breast during milk expression.
Figure 22B:
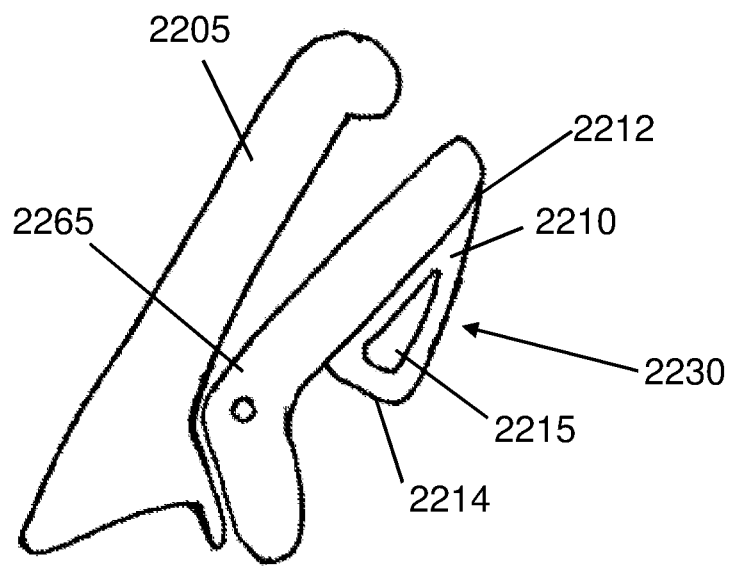

FIGS. 22A-22B illustrate another exemplary mechanism for creating posterior compression of the breast during milk expression. A flange 2205 of a breast interface may comprise a fluid pocket 2210 disposed near a distal end thereof. The fluid pocket may be coupled to a movable member or lever 2265 such as any lever as described herein, or the fluid pocket may be coupled directly to an internal surface of the flange. The fluid pocket may be filled with an incompressible fluid 2215, and configured to transition between a resting configuration and an expression configuration. FIG. 22A shows the fluid pocket in the resting configuration 2220. In the resting configuration, the height of the fluid pocket is greater at its distal end 2212 than at its proximal end 2214. When vacuum pressure pulls a breast into the breast interface, the breast compresses against the fluid pocket starting at the distal end of the fluid pocket. This compression causes the fluid to be compressed out of the distal end and towards the proximal end, such that the fluid pocket undergoes a change in shape, transitioning to the expression configuration 2230 shown in FIG. 22B. In the expression configuration, the height of the fluid pocket is greater at the proximal end than at the distal end. When the vacuum pressure is released, the fluid pocket can return to the resting configuration of FIG. 22A. The change in shape of the fluid pocket due to the movement of the fluid during compression by the breast can help create additional peristaltic compression at the posterior portions of the breast. When the fluid pocket is incorporated into a posterior compression lever as shown in FIGS. 22A-22B, the fluid pocket can enhance the posterior compression created by the lever.

Experimental Data

Figure 14:
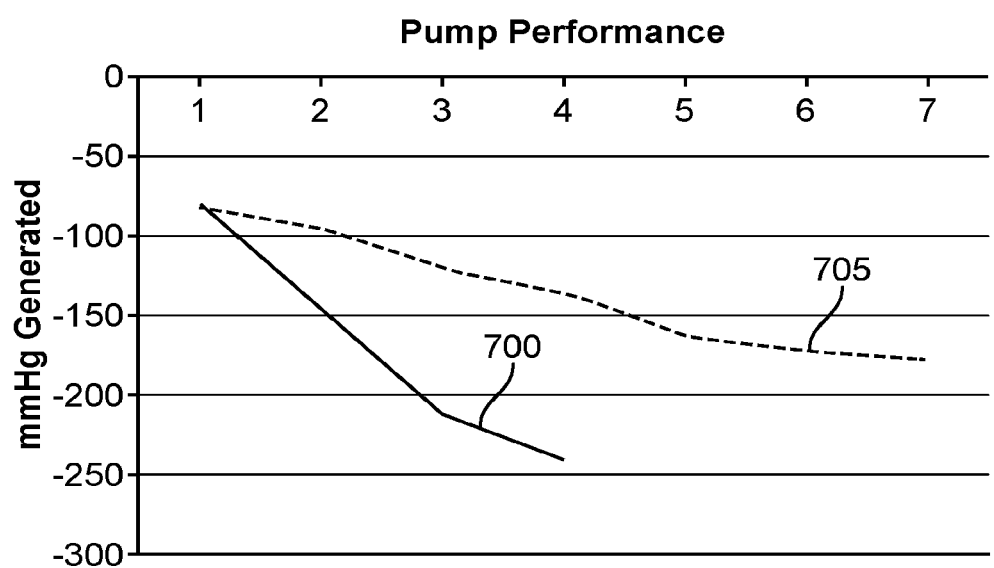
FIG. 14 is a graph illustrating the pump performance of an exemplary embodiment compared to a commercial device.
Figure 15:
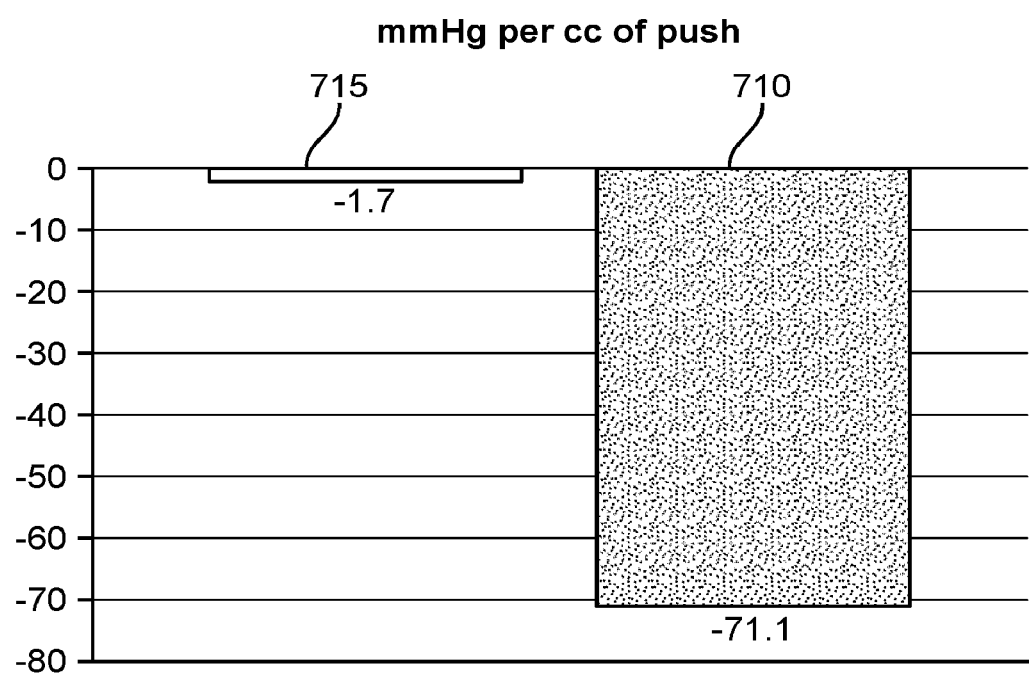
FIG. 15 is a graph illustrating the pumping efficiency of an exemplary embodiment compared to a commercial device.

FIGS. 14 and 15 illustrate experimental pumping data obtained from a commercial breast pump device and an exemplary embodiment of the present invention. The exemplary embodiment utilized an incompressible fluid for pumping and had a maximum hydraulic fluid volume of 4 cc, while the commercial device utilized air for pumping and had a maximum volume of 114 cc.

FIG. 14 illustrates a graph of the pump performance as quantified by vacuum pressure generated per run. For the exemplary embodiment, pressure measurements were taken for 1 cc, 2 cc, 3 cc, and 4 cc of fluid volume displaced by the pump, with the run number corresponding to the volume in cc. For the commercial device, measurements were taken with the pump set to one of seven equally incremented positions along the vacuum adjustment gauge representing 46 cc, 57 cc, 68 cc, 80 cc, 91 cc, 103 cc, and 114 cc of fluid volume displaced by the pump, respectively, with the run number corresponding to the position number. Curve 700 corresponds to the exemplary embodiment and curve 705 corresponds to the commercial device. The exemplary embodiment generated higher levels of vacuum pressure per displacement volume compared to the commercial device, with maximum vacuum pressures of −240.5 mmHg and −177.9 mmHg, respectively.

FIG. 15 illustrates a graph of the pump efficiency as measured by the maximum vacuum pressure per maximum volume of fluid displaced, with bar 710 corresponding to the exemplary embodiment and bar 715 corresponding to the commercial device. The exemplary embodiment demonstrated a 42-fold increase in pumping efficiency compared to the commercial device, with efficiencies of −71.1 mmHg/cc and −1.7 mmHg/cc, respectively.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A device for expression of breast milk from a breast, the device comprising:
    a breast interface comprising a flange configured to engage the breast and fluidly seal thereagainst; and
    an actuatable assembly operably coupled to the breast interface and configured to generate negative pressure at the breast interface when actuated,
    wherein the flange comprises a movable member configured to engage an anterior portion of the breast and a posterior portion of the breast when the breast is fluidly sealed against the flange,
    wherein the movable member is substantially rigid and configured to apply anterior compression to an anterior portion of the breast in response to generation of negative pressure at the breast interface, and
    wherein the movable member is configured to move in response to anterior compression of the breast against the movable member, to subsequently apply posterior compression to a posterior portion of the breast with the movable member.

2. The device as in claim 1, wherein first arm of the movable member is configured to move away from the breast and the second arm of the movable member is configured to move towards the breast in response to generation of the negative pressure at the breast interface.

3. The device as in claim 1, wherein the movable member is configured to apply the anterior compression and the posterior compression in a temporally coupled manner, such that, when the negative pressure is applied at the breast interface, the anterior compression is applied first and the posterior compression is applied second.

4. The device as in claim 1, wherein the movable member is a lever, the lever configured to rotate about a pivot point to apply the posterior compression to the breast.

5. The device as in claim 4, wherein the lever is coupled to an interior surface of the flange via the pivot point.

6. The device as in claim 5, wherein the anterior portion of the lever comprises a first arm of the lever and the posterior portion of the lever comprises a second arm of the lever, the first and second arms joined about the pivot point, wherein the first arm is configured to apply the anterior compression and the second arm is configured to apply the posterior compression to the breast.

7. The device as in claim 6, wherein the lever is configured such that greater moment is applied to the first arm than to the second arm when the breast compresses against the lever.

8. The device as in claim 6, wherein a longitudinal axis of the first arm and a longitudinal axis of the second arm are non-collinear.

9. The device as in claim 6, wherein a length of the first arm is different from a length of the second arm.

10. The device as in claim 4, wherein the lever comprises a substantially rigid member of the flange coupled to a flexible member of the flange, and wherein the substantially rigid member of the flange is configured to rotate about the pivot point, disposed near an anterior portion of the substantially rigid member, to apply the posterior compression.

11. The device as in claim 10, wherein the flexible member comprises an anterior portion configured to bend in response to compression of the breast against the lever, and wherein the substantially rigid member is configured to rotate about the pivot point in response to the bending of the anterior portion of the flexible member.

12. The device as in claim 4, further comprising a flexible cover disposed over the lever to enclose the lever, the flexible cover configured to fluidly seal against the breast and to allow rotation of the lever within the cover, thereby reducing pinching of the breast by the lever during rotation.

13. The device as in claim 1, wherein the anterior compression causes retrograde flow of at least a portion of milk in a milk duct of the breast in a direction away from a nipple of the breast, and wherein the posterior compression reduces the retrograde flow of milk.

14. The device as in claim 1, wherein the flange comprises a plurality of additional movable members distributed annularly about the flange.

15. The device as in claim 1, wherein the movable member comprises a single, continuous movable member extending annularly about the flange.

16. The device as in claim 1, wherein the breast interface further comprises a housing and a membrane disposed within and coupled to the housing, wherein the membrane comprises an expandable portion configured to move toward the housing and away from the breast in response to actuation of the actuatable assembly to apply negative pressure at the breast interface.

17. The device as in claim 16, wherein the membrane comprises a flexible cover portion disposed over the movable member to enclose the movable member, the flexible cover portion configured to fluidly seal against the breast and to allow movement of the movable member within the flexible cover portion.

18. The device as in claim 16, wherein the membrane is shaped to form the flange, wherein the movable member comprises a substantially rigid portion of the flange, and wherein the substantially rigid portion of the flange comprises a thickness that is greater than a thickness of the membrane at the expandable portion.

19. The device as in claim 18, wherein the substantially rigid portion of the flange is configured to rotate about a pivot point disposed near an anterior portion of the substantially rigid portion of the flange, thereby applying the posterior compression to the breast.

\* \* \* \* \*